(12) United States Patent
Gao et al.

(10) Patent No.: US 12,371,710 B2
(45) Date of Patent: Jul. 29, 2025

(54) MODIFIED AAV CONSTRUCTS AND USES THEREOF

(71) Applicant: University of Massachusetts, Westborough, MA (US)

(72) Inventors: Guangping Gao, Worcester, MA (US); Jun Xie, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 1164 days.

(21) Appl. No.: 17/054,794

(22) PCT Filed: May 15, 2019

(86) PCT No.: PCT/US2019/032505
§ 371 (c)(1),
(2) Date: Nov. 12, 2020

(87) PCT Pub. No.: WO2019/222413
PCT Pub. Date: Nov. 21, 2019

(65) Prior Publication Data
US 2021/0222196 A1    Jul. 22, 2021

Related U.S. Application Data

(60) Provisional application No. 62/671,908, filed on May 15, 2018.

(51) Int. Cl.
*C12N 15/86*    (2006.01)
*A61K 35/76*    (2015.01)
*C12N 15/11*    (2006.01)
*C12N 15/113*   (2010.01)

(52) U.S. Cl.
CPC .............. *C12N 15/86* (2013.01); *A61K 35/76* (2013.01); *C12N 15/111* (2013.01); *C12N 15/113* (2013.01); *C12N 2310/141* (2013.01); *C12N 2320/32* (2013.01); *C12N 2750/14143* (2013.01)

(58) Field of Classification Search
CPC ..... C12N 15/86; C12N 15/111; C12N 15/113; C12N 2310/141; C12N 2320/32; C12N 2750/14143; C12N 2310/14; C12N 2320/50; A61K 35/76
See application file for complete search history.

(56) References Cited

U.S. PATENT DOCUMENTS 11,046,955 B2 *  6/2021  Gao ..................... A61K 31/713
2017/0355989 A1  12/2017  Konstantinova et al.

FOREIGN PATENT DOCUMENTS

WO  WO-2015031392 A1 *  3/2015  ......... A61K 31/7105
WO  WO-2016172008 A1 *  10/2016  ........... A61K 31/713
WO  WO 2018/057855 A1    3/2018

OTHER PUBLICATIONS

Bonamichi, B. D. S. F., Parente, E. B., Dos Santos, R. B., Beltzhoover, R., Lee, J., & Salles, J. N. (2018). The challenge of obesity treatment: a review of approved drugs and new therapeutic targets. J Obes Eat Disord, 4(1), 1-10. (Year: 2018).*
Sweeting, A. N., Hocking, S. L., & Markovic, T. P. (2015). Pharmacotherapy for the treatment of obesity. Molecular and cellular endocrinology, 418, 173-183. (Year: 2015).*
Partial European Search Report for Application No. 19803735.0, mailed Mar. 14, 2022.
Extended European Search Report for Application No. 19803735.0, mailed Jun. 14, 2022.
Calloni et al., Scaffolds for Artificial miRNA Expression in Animal Cells. Hum Gene Ther Methods. Oct. 2015;26(5):162-74. doi: 10.1089/hgtb.2015.043. Epub Sep. 25, 2015.
Galka-Marciniak et al., siRNA release from pri-miRNA scaffolds is controlled by the sequence and structure of RNA. Biochim Biophys Acta. Apr. 2016;1859(4):639-49. doi: 10.1016/j.bbagrm.2016.02.014. Epub Feb. 26, 2016.
Nejati et al., The Effect of Different microRNA Backbones on Artificial miRNA Expression and Knockdown Activity Against HIV-1 Replication. Microrna. 2016;5(2):146-151. doi: 10.2174/2211536605666160708235058.
Pfister et al., Safe and Efficient Silencing with a Pol II, but Not a Pol III, Promoter Expressing an Artificial miRNA Targeting Human Huntingtin. Mol Ther Nucleic Acids. Jun. 16, 2017:7:324-334. doi: 10.1016/j.omtn.2017.04.011. Epub Apr. 14, 2017.
International Search Report and Written Opinion for Application No. PCT/US2019/032505, mailed Aug. 30, 2019.
International Preliminary Report on Patentability for Application No. PCT/US2019/032505, mailed Nov. 26, 2020.
Gagnon et al., Proprotein convertase 1/3 (PC1/3) in the rat alveolar macrophage cell line NR8383: localization, trafficking and effects on cytokine secretion. PLoS One. Apr. 24, 2013;8(4):e61557. doi: 10.1371/journal.pone.0061557.

* cited by examiner

Primary Examiner — Richard A Schnizer
Assistant Examiner — Christina Tran
(74) Attorney, Agent, or Firm — Wolf, Greenfield & Sacks, P.C.

(57) ABSTRACT

In some aspects the disclosure relates to recombinant adeno-associated virus (rAAV) vectors and rAAVs (e.g., viral particles) engineered to express a transgene comprising an inhibitory nucleic acid (e.g., an artificial miRNA, amiRNA) having a pri-miRNA scaffold and a guide strand that targets a human target gene.

8 Claims, 16 Drawing Sheets

Specification includes a Sequence Listing.

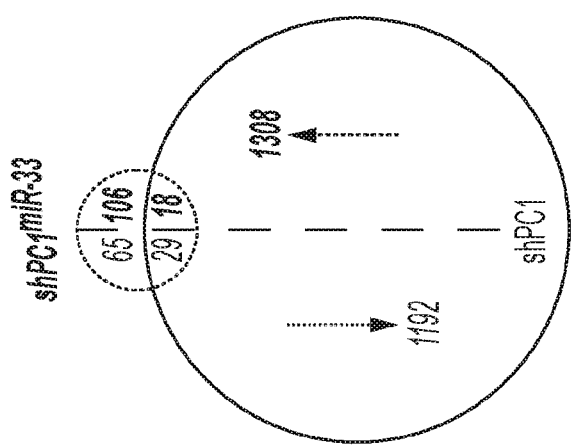

SEQUENCE LISTING

<160> NUMBER OF SEQ ID NOS: 81

<210> SEQ ID NO 1
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 1
catcatcaat tcgagcaga attcaagaga ttctgctcga aattgatgat gttttt    56

<210> SEQ ID NO 2
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 2
cgggattcta ccagatatct attcaagaga tagatatctg gtagaatccc gttttt    56

<210> SEQ ID NO 3
<211> LENGTH: 286
<212> TYPE: DNA
<213> ORGANISM: Artificial Sequence
<220> FEATURE:
<223> OTHER INFORMATION: Synthetic polynucleotide

<400> SEQUENCE: 3
agatctaggg ctctgcgttt gctccaggta gtccgctgct cccttgggcc tgggcccact    60
gacagccctg gtgcctctgg ccggctgcac acctcctggc gggcagctgt gttctgctcg    120
aaattgatga tgtgttctgg caatacctgc atcatcatat ccgagcagaa cacggaggcc    180
tgccctgact gcccacggtg ccgtggccaa agaggatcta agggcaccgc tgagggccta    240
cctaaccatc gtggggaata aggacagtgt caccctttt ctgcag    286

<210> SEQ ID NO 4
<211> LENGTH: 286
<212> TYPE: DNA
<213> ORGANISM: Artificial Sequence
<220> FEATURE:

```
<223> OTHER INFORMATION: Synthetic polynucleotide

<400> SEQUENCE: 4
agatctaggg ctctgcgttt gctccaggta gtccgctgct cccttgggcc tgggcccact      60
gacagccctg gtgcctctgg ccggctgcac acctcctggc gggcagctgt gtagatatct     120
ggtagaatcc cgtgttctgg caatacctgc gggattcgcc aagatatcta cacggaggcc     180
tgccctgact gcccacggtg ccgtggccaa agaggatcta agggcaccgc tgagggccta     240
cctaaccatc gtggggaata aggacagtgt cacccttttt ctgcag                    286

<210> SEQ ID NO 5
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 5
atcgggcccg actgcagttt cagcgtttg                                        29

<210> SEQ ID NO 6
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 6
cgcgggcccg actttacatt acacacaat                                        29

<210> SEQ ID NO 7
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 7
agggctctgc gtttgctcca gg                                               22

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
agggtgacac tgtccttatt                                                  20

<210> SEQ ID NO 9
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 9
gccccttctc tttggcag                                                    18

<210> SEQ ID NO 10
<211> LENGTH: 17
<212> TYPE: DNA
<213> ORGANISM: Artificial Sequence
```

```
<220> FEATURE:
<223> OTHER INFORMATION: Synthetic polynucleotide

<400> SEQUENCE: 10
ttggccagca agcttgg                                                    17

<210> SEQ ID NO 11
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 11
ggaaggcatt gtgggcgta a                                                21

<210> SEQ ID NO 12
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 12
tgcaaagtct ctggctgtc                                                  19

<210> SEQ ID NO 13
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 13
atttcaggtc gtcccatatg tc                                              22

<210> SEQ ID NO 14
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 14
gtccctcacc ttccggatga tag                                             23

<210> SEQ ID NO 15
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 15
ctcagtcctg ggcctacttt ttcca                                           25

<210> SEQ ID NO 16
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 16
tgccacgtca gaagagttca g                                               21
```

<210> SEQ ID NO 17
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 17
ggattcccag cctttaaaat atttac                                26

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
ggattaaaag atccatgaag                                       20

<210> SEQ ID NO 19
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 19
gatatcgact gttggcatta agcccc                                26

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 20
gactttccaa gtctcacaag                                       20

<210> SEQ ID NO 21
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 21
accgcggtgc tcaggtgaga g                                     21

<210> SEQ ID NO 22
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 22
cagagactga gcacggt                                          17

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucleotide -continued

```
<400> SEQUENCE: 23 tttttgcctcc atccagaagt gc                                             22

<210> SEQ ID NO 24
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 24
ggaagagtgg tgaacacagg a                                               21

<210> SEQ ID NO 25
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 25
agtctgggta ccccacctcc agag                                            24

<210> SEQ ID NO 26
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 26
gcacagtgaa gaggaaaatg taccc                                           25

<210> SEQ ID NO 27
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 27
aggtacaggc taggtcttgt cc                                              22

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
agctccgtgc tccgtagtct                                                 20

<210> SEQ ID NO 29
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 29
gtgtttgaca cttagtagat ga                                              22

<210> SEQ ID NO 30
```

```
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
aatatatttc tttgcttagc                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
tttctctttg caggtgctgc                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 32
gtctgacatc tacgttcatc                                              20

<210> SEQ ID NO 33
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 33
tgactttcat ctgtactaca ttcaagagat gtagtacaga tgaaagtcag cttttt      56

<210> SEQ ID NO 34
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 34
cgcctcgaga aattgaagaa gatctgttaa c                                 31

<210> SEQ ID NO 35
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 35
cgcgcggccg ctcttctctg gaggggactg t                                 31

<210> SEQ ID NO 36
<211> LENGTH: 33
<212> TYPE: DNA
<213> ORGANISM: Artificial Sequence
<220> FEATURE:
<223> OTHER INFORMATION: Synthetic polynucleotide
```

```
<400> SEQUENCE: 36
cgcctcgagc ccaaaatgaa tgcttctttc tcg                                    33

<210> SEQ ID NO 37
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 37
cgcgcggccg ccctgaagaa tctggttctt c                                      31

<210> SEQ ID NO 38
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 38
ataactcgag cgaaggccgt gtgcgtgctg aagggc                                 36

<210> SEQ ID NO 39
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 39
gccagcggcc gcttgggcga tcccaattac accacaag                               38

<210> SEQ ID NO 40
<211> LENGTH: 286
<212> TYPE: DNA
<213> ORGANISM: Artificial Sequence
<220> FEATURE:
<223> OTHER INFORMATION: Synthetic polynucleotide

<400> SEQUENCE: 40
agatctaggg ctctgcgttt gctccaggta gtccgctgct cccttgggcc tgggcccact       60
gacagccctg gtgcctctgg ccggctgcac acctcctggc gggcagctgt gtgtagtaca      120
gatgaaagtc agtgttctgg caatacctgc tgactttact atgtactaca cacggaggcc      180
tgccctgact gccacggtg ccgtggccaa agaggatcta agggcaccgc tgagggccta       240
cctaaccatc gtggggaata aggacagtgt cacccttttt ctgcag                     286

<210> SEQ ID NO 41
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 41
gtccaggttg aatcacgggt                                                   20

<210> SEQ ID NO 42
<211> LENGTH: 20
<212> TYPE: DNA
<213> ORGANISM: Artificial Sequence
<220> FEATURE:
```

<223> OTHER INFORMATION: Synthetic polynucleotide

<400> SEQUENCE: 42
aggatcctgc aaggtcaagc                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 43
aaaggccgct gctttgaaag                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 44
ccgcacctga atttgttgca                                               20

<210> SEQ ID NO 45
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 45
atgccaacac agtgctgtct gg                                            22

<210> SEQ ID NO 46
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 46
tgcttgctga tccacatctg ct                                            22

<210> SEQ ID NO 47
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 47
agcaaagacc ccaacgagaa                                               20

<210> SEQ ID NO 48
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 48
ggcggcggtc acgaa                                                    15

```
<210> SEQ ID NO 49
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 49
cgcgatcaca tggtcctgct gg                                            22

<210> SEQ ID NO 50
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 50
gactttcatc tgtactaca                                                19

<210> SEQ ID NO 51
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 51
ctctgtatcg ttccaatttt agtata                                        26

<210> SEQ ID NO 52
<211> LENGTH: 111
<212> TYPE: DNA
<213> ORGANISM: Artificial Sequence
<220> FEATURE:
<223> OTHER INFORMATION: Synthetic polynucleotide

<400> SEQUENCE: 52
ugcacaccuc cuggcgggca gcugugguqc auuguaguug cauugcaugu ucuggcaaua    60
ggcgugcaau guuuccacag ugcaucacgg aggcctgccc ugacugccca c            111

<210> SEQ ID NO 53
<211> LENGTH: 53
<212> TYPE: RNA
<213> ORGANISM: Artificial Sequence
<220> FEATURE:
<223> OTHER INFORMATION: Synthetic polynucleotide

<400> SEQUENCE: 53
cugacuuuca ucuguacuac auucaagaga uguaguacag augaaaguca guu           53

<210> SEQ ID NO 54
<211> LENGTH: 111
<212> TYPE: RNA
<213> ORGANISM: Artificial Sequence
<220> FEATURE:
<223> OTHER INFORMATION: Synthetic polynucleotide

<400> SEQUENCE: 54
ugcacaccuc cuggcgggca gcugugugua guacagauga aagucagugu ucuggcaaua    60 ccguggacu uuacuuugua cuacacacgg aggccugccc ugacugccca c              111

<210> SEQ ID NO 55
<211> LENGTH: 59
<212> TYPE: RNA
```

<213> ORGANISM: Artificial Sequence
<220> FEATURE:
<223> OTHER INFORMATION: Synthetic polynucleotide

<400> SEQUENCE: 55
ucucgggauu cuaccagaua ucuauucaag agauagauau cugguagaau cccguuuuu    59

<210> SEQ ID NO 56
<211> LENGTH: 99
<212> TYPE: RNA
<213> ORGANISM: Artificial Sequence
<220> FEATURE:
<223> OTHER INFORMATION: Synthetic polynucleotide

<400> SEQUENCE: 56
ccuggcgggc agcuguguag auaucuggua gaaucccgug uucggcaauu ccgugggauu    60
cgccuagauc uauacacgga ggccugcccu gacugccca                          99

<210> SEQ ID NO 57
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 57
tcctttcaga tgtcataact tcaagagatg tagtacagat gaaagtc                 47

<210> SEQ ID NO 58
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 58
tcctttcaga tgtcatacat tcaagagatg tagtacagat gaaagtc                 47

<210> SEQ ID NO 59
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 59
tcctttcatc tgtcataact tcaagagatg tagtacagat gaaagtc                 47

<210> SEQ ID NO 60
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 60
gactttcaga tgtcataact tcaagagatg tagtacagat gaaagtc                 47

<210> SEQ ID NO 61
<211> LENGTH: 47
<212> TYPE: DNA
<213> ORGANISM: Artificial Sequence
<220> FEATURE:
<223> OTHER INFORMATION: Synthetic polynucleotide

```
<400> SEQUENCE: 61
tcctttcaga tgtactacat tcaagagatg tagtacagat gaaagtc         47

<210> SEQ ID NO 62
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 62
gactggcaga tgtactacat tcaagagatg tagtacagat gaaagtc         47

<210> SEQ ID NO 63
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 63
tcctttcatc tgtcatacat tcaagagatg tagtacagat gaaagtc         47

<210> SEQ ID NO 64
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 64
gactttcaga tgtcatacat tcaagagatg tagtacagat gaaagtc         47

<210> SEQ ID NO 65
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 65
tcctttcatc tgtactaact tcaagagatg tagtacagat gaaagtc         47

<210> SEQ ID NO 66
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 66
gactggcatc tgtactaact tcaagagatg tagtacagat gaaagtc         47

<210> SEQ ID NO 67
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 67
gactttcaga tgtactaact tcaagagatg tagtacagat gaaagtc         47

<210> SEQ ID NO 68
```

```
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 68
gactttcatc tgtcataact tcaagagatg tagtacagat gaaagtc          47

<210> SEQ ID NO 69
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 69
gactttcatc tgtactacat tcaagagatg tagtacagat gaaagag          47

<210> SEQ ID NO 70
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 70
ctctttcatc tgtactacat tcaagagatg tagtacagat gaaagtc          47

<210> SEQ ID NO 71
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 71
tcctttcatc tgtactacat tcaagagatg tagtacagat gaaagtc          47

<210> SEQ ID NO 72
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 72
gactggcatc tgtactacat tcaagagatg tagtacagat gaaagtc          47

<210> SEQ ID NO 73
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 73
gactttcaga tgtactacat tcaagagatg tagtacagat gaaagtc          47

<210> SEQ ID NO 74
<211> LENGTH: 47
<212> TYPE: DNA
<213> ORGANISM: Artificial Sequence
<220> FEATURE:
<223> OTHER INFORMATION: Synthetic polynucleotide
```

<400> SEQUENCE: 74
gactttcatc tgtcatacat tcaagagatg tagtacagat gaaagtc                47

<210> SEQ ID NO 75
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 75
gactttcatc tgtactaact tcaagagatg tagtacagat gaaagtc                47

<210> SEQ ID NO 76
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 76
gactttcatc tgtactacat tcaagagatg tagtacagat gaaagtc                47

<210> SEQ ID NO 77
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 77
gactttcatc tgtactacat tcaagagatg tagtacagat gaaagtc                47

<210> SEQ ID NO 78
<211> LENGTH: 106
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(11)
<223> OTHER INFORMATION: n is a, c, g, or u
<220> FEATURE:
<221> NAME/KEY: misc_feature
<222> LOCATION: (14)..(18)
<223> OTHER INFORMATION: n is a, c, g, or u
<220> FEATURE:
<221> NAME/KEY: misc_feature
<222> LOCATION: (22)..(46)
<223> OTHER INFORMATION: n is a, c, g, or u
<220> FEATURE:
<221> NAME/KEY: misc_feature
<222> LOCATION: (51)..(59)
<223> OTHER INFORMATION: n is a, c, g, or u
<220> FEATURE:
<221> NAME/KEY: misc_feature
<222> LOCATION: (61)..(85)
<223> OTHER INFORMATION: n is a, c, g, or u
<220> FEATURE:
<221> NAME/KEY: misc_feature
<222> LOCATION: (89)..(93)
<223> OTHER INFORMATION: n is a, c, g, or u
<220> FEATURE:
<221> NAME/KEY: misc_feature
<222> LOCATION: (95)..(99)
<223> OTHER INFORMATION: n is a, c, g, or u
<220> FEATURE:
<221> NAME/KEY: misc_feature
<222> LOCATION: (104)..(106)

```
<223> OTHER INFORMATION: n is a, c, g, or u

<400> SEQUENCE: 78
nnnnnnnnnn nugnnnnncu cnnnnnnnnn nnnnnnnnnn nnnnnnugug nnnnnnnnna      60
nnnnnnnnnn nnnnnnnnnn nnnnngcgnn nnncnnnnnc gucnnn                    106

<210> SEQ ID NO 79
<211> LENGTH: 111
<212> TYPE: DNA
<213> ORGANISM: Artificial Sequence
<220> FEATURE:
<223> OTHER INFORMATION: Synthetic polynucleotide

<400> SEQUENCE: 79
ugcacaccuc cuggcgggca gcugggugc auuguaguug cauugcaugu ucuggcaaua       60
ccugugcaau guuuccacag ugcaucacgg aggcctgccc ugacugccca c             111

<210> SEQ ID NO 80
<211> LENGTH: 109
<212> TYPE: DNA
<213> ORGANISM: Artificial Sequence
<220> FEATURE:
<223> OTHER INFORMATION: Synthetic polynucleotide

<400> SEQUENCE: 80
ugcacaccuc cuggcgggcu cuguggugca uuguaguugc auugcaugug cuggcaauac      60
cugugcaaug uuuccacagu gcaucacggc gcctgcccug accguccac                109

<210> SEQ ID NO 81
<211> LENGTH: 109
<212> TYPE: DNA
<213> ORGANISM: Artificial Sequence
<220> FEATURE:
<223> OTHER INFORMATION: Synthetic polynucleotide

<400> SEQUENCE: 81
ugcacaccuc cuggcgggcu cuguggugca uuguaguugc auugcaugug cuggcaauac      60
cugugcaaug uaacuacagu gcaucacggc gcctgcccug accguccac                109
```

MODIFIED AAV CONSTRUCTS AND USES THEREOF

RELATED APPLICATIONS

This Application is a national stage filing under 35 U.S.C. § 371 of international PCT application, PCT/US2019/032505, filed May 15, 2019, which claims priority under 35 U.S.C. § 119(e) to U.S. provisional patent application, U.S. Ser. No. 62/671,908, filed May 15, 2018, the entire contents of each of which are incorporated herein by reference.

GOVERNMENT SUPPORT

This invention was made with government support under NS076991, AI100263, HL131471, and HL097088, awarded by the National Institutes of Health. The government has certain rights in the invention.

REFERENCE TO AN ELECTRONIC SEQUENCE LISTING

The contents of the electronic sequence listing (U012070108US01-SEQ-KZM.txt; Size: 18,397 bytes; and Date of Creation: Nov. 12, 2020) is herein incorporated by reference in its entirety.

BACKGROUND

High levels of AAV-delivered short-hairpin RNAs (shRNAs) can perturb the RNA interference (RNAi) machinery, leading to cellular toxicity. Reducing the amount of shRNA by lowering vector doses, selecting less efficient Adeno-associated (AAV) serotypes, or using weaker Pol II promoters instead of strong, constitutive H1 or U6 Pol III promoter, have been used to reduce toxicity. However, each of these strategies has thus far been observed to negatively impact RNAi potency.

SUMMARY

Aspects of the disclosure relate to isolated nucleic acids and recombinant Adeno-associated viruses (rAAVs) engineered to express a transgene comprising an inhibitory RNA guide strand (e.g., a guide strand targeting a human gene) inserted into an artificial miRNA scaffold (e.g., a scaffold derived from a mouse pri-miRNA, such as a mouse pri-miRNA-33). The disclosure is based, in part, on compositions which improve genomic integrity of rAAV vectors, and, in some embodiments, achieve a reduction in off-target gene silencing while maintaining effective gene knockdown.

Accordingly, in some aspects, the disclosure provides in some aspects, the disclosure provides an isolated nucleic acid encoding a transgene engineered to express an inhibitory nucleic acid comprising a mouse pri-miRNA scaffold; and a guide strand targeting a human gene.

In some embodiments, a pri-miRNA scaffold is selected from pri-miR-122, pri-miR-33, pri-miR-26a, pri-miR-126, pri-miR-22, pri-miR-199, pri-miR-99, pri-miR-21, pri-miR-375, pri-miR-101, pri-miR-451, pri-miR-194, pri-miR-30a, and pri-miR-155.

In some embodiments, a guide strand targets SOD1 or PC-1.

In some embodiments, a transgene comprises a promoter operably linked to a nucleic acid sequence encoding the inhibitory nucleic acid. In some embodiments, a promoter is a RNA polymerase III (Pol III) promoter. In some embodiments, a Pol III promoter is a U6 promoter or an H1 promoter. In some embodiments, a promoter is a RNA polymerase II promoter. In some embodiments, a Pol II promoter comprises a chicken beta-actin (CBA) promoter.

In some embodiments, a transgene is engineered to express a protein. In some embodiments, the protein is a therapeutic protein. In some embodiments, therapeutic protein is SOD1 or PC-1. In some embodiments, the protein is a detectable label, for example GFP or RFP.

In some embodiments, a transgene is flanked by adeno-associated virus (AAV) inverted terminal repeats (ITRs). In some embodiments, at least one ITR is a mutant ITR (mTR).

In some aspects, the disclosure provides a recombinant adeno-associated virus (rAAV) comprising: an isolated nucleic acid as described herein; and an AAV capsid protein.

In some aspects, the disclosure provides an rAAV vector comprising a transgene engineered to express an inhibitory nucleic acid comprising a pri-miRNA scaffold; and a guide strand that targets SOD1.

In some aspects, the disclosure provides an rAAV vector comprising a transgene engineered to express an inhibitory nucleic acid comprising a pri-miRNA scaffold; and a guide strand that targets PC-1.

In some embodiments, a pri-miRNA scaffold is selected from pri-miR-122, pri-miR-33, pri-miR-26a, pri-miR-126, pri-miR-22, pri-miR-199, pri-miR-99, pri-miR-21, pri-miR-375, pri-miR-101, pri-miR-451, pri-miR-194, pri-miR-30a, and pri-miR-155. In some embodiments, the pri-miRNA scaffold is a mouse pri-miRNA33 scaffold.

In some embodiments, a guide strand that targets SOD1 is encoded by an isolated nucleic acid comprising the sequence set forth in SEQ ID NO: 1. In some embodiments, a transgene comprises the sequence set forth in SEQ ID NO: 3.

In some embodiments, a guide strand that targets PC-1 is encoded by an isolated nucleic acid comprising the sequence set forth in SEQ ID NO: 2. In some embodiments, a transgene comprises the sequence set forth in SEQ ID NO: 4.

In some embodiments, an rAAV vector is a self-complementary AAV (scAAV) vector.

In some aspects, the disclosure provides an rAAV comprising an rAAV vector as described herein. In some embodiments, the rAAV comprises an AAV9 capsid protein.

In some aspects, the disclosure provides a method of reducing expression of a target gene in a cell, the method comprising administering an isolated nucleic acid or the rAAV as described herein, to the cell.

In some embodiments, a target gene is SOD1 or PC-1. In some embodiments, a cell is in a subject.

In some aspects, the disclosure provides a method for treating amyotrophic lateral sclerosis (ALS) in a subject in need thereof, the method comprising administering to the subject an isolated nucleic acid or rAAV as described herein. In some embodiments, a subject is a human.

In some embodiments, a subject is characterized as having one or more mutations in a SOD1 gene.

In some aspects, the disclosure provides a method of treating obesity in a subject in need thereof, the method comprising administering to the subject an isolated nucleic acid or rAAV as described herein. In some embodiments, a subject is a human.

In some embodiments, administration is via injection. In some embodiments, injection is intravenous injection.

BRIEF DESCRIPTION OF DRAWINGS

FIG. 1A shows viral genome of scAAV8 vectors carrying pri-miRNA fragments which contain pre-miRNA and ~100 base pairs flanking sequences at each end. Representative 1% agarose gel of viral genomes isolated from packaged vectors. FIG. 1B shows design of artificial miRNA constructs using miR-33 scaffold as an example. The secondary structure of mmu-pre-miR-33 was adapted from miRBase (mirbase.org/cgi-bin/mirna_entry.pl?acc=MI0000707). SEQ ID NOs: 52-54 are shown top to bottom. FIG. 1C shows a comparison of gene silencing efficiency in HEK293 cells by measuring the relative β-Gal activity. Plasmids expressing RNA inhibitors were co-transfected with sensor plasmid into HEK293 cells at the indicated amount. FIG. 1D shows agarose gel analysis of viral DNA from purified vectors that carry no shRNA (CTRL), shApob, artificial miR-155, or miR-33 against Apob (shApobmiR-155 or shApobmiR-33). FIG. 1E shows relative β-Gal activity in HEK293 cells transfected with PC-1 and SOD1 inhibitors and their sensor plasmids. FIG. 1F is a schematic of PC-1 gene silencing constructs used for AAV packaging. FIG. 1G shows an agarose gel analysis of viral DNA extracted from purified vectors that were packaged into AAV9. Purple arrows indicate truncated genomes. FIG. 1H shows qRT-PCR analysis of PC-1 mRNA in the liver of mice received rAAV9-shPC-1 or rAAV9-shPC-1miR-33. Five mice in the $1.0 \times 10^{11}$ GCs/mouse group and four mice in the $3.0 \times 10^{10}$ GCs/mouse group. GC, genome copy. FIG. 1I shows qRT-PCR analysis of Apob mRNA in the liver of mice (n=5 in each group) received rAAV9-shApob or rAAV9-shApobmiR-33. rAAVs at the indicated doses were injected to adult C57/b6 mice by tail vein. After three weeks, mice were sacrificed for PC-1 and Apob gene expression analysis using qRT-PCR. Values are mean±SD.

FIGS. 2A-2D show small RNA and transcriptome analysis in mouse liver. Adult C57/b6 mice received $1.0 \times 10^{11}$ GCs rAAV9 without RNA inhibitor, shPC-1, or shPC-1miR-33 from tail vein. After three weeks, mice were sacrificed and liver RNA was extracted used for the following small silencing RNA (FIG. 2A), endogenous miRNA (FIG. 2B), and global gene expression analyses (FIG. 2C). FIG. 2A shows profiling of 5' and 3' distribution of guide and passenger strands of silencing RNA detected in mice by small-RNA-Seq (mean±SD, n=3). SEQ ID NOs: 55 and 56 are shown left to right. FIG. 2B shows a scatter plot comparing the abundance of endogenous miRNAs and small RNAs expressed by AAV. Each point represents the normalized miRNA reads (in Parts per Million) averaged from three biological replicates. Error bar represents standard deviation (n=3). FIG. 2C shows a comparison of mRNA abundance in whole transcriptome analysis. Each point represents the mean FPKM value of a single gene (n=3). Significantly dysregulated mRNAs are represented in blue dots. Genes of small RNA pathway are annotated with open circles (no change) or closed dots (significantly changed). The PC-1 is annotated with solid black dot. FIG. 2D shows a Venn diagram showing the differentially expressed gene in shPC-1miR-33 and shPC-1 treated mice.

FIG. 3A shows a schematic and sequence alignment of one embodiment of a self-complementary (sc) AAV construct carrying shApob encoding sequence in the intronic region between the CB (CMV enhancer/chicken β-actin, CB) promoter and EGFP gene. Nucleotide mismatches are in grey. SEQ ID NOs: 57-77 are shown top to bottom. FIG. 3B shows a southern blot analysis of low-molecular DNA extracted from HEK293 transfected with the scAAV-shApob plasmid, pRep2/Cap9 plasmid, and pAdeno-helper plasmid using 32P-labeled EGFP probe. FIG. 3C shows data indicating a correlation between the thermodynamic stabilities of short hairpin DNA and their ratios of truncated AAV genome to full-length genomes. The dG values were calculated by RNAfold. FIG. 3D shows ratios of β-galactosidase (β-Gal) and Fire-fly luciferase (Fluc) in HEK293 cells co-transfected with shApob constructs and a sensor plasmid carrying the Apob coding sequence in the 3'UTR of β-Gal. After 48 hours, Fluc and β-Gal levels were measured and the ratio between β-Gal and Fluc was calculated to reflect the gene silencing efficacies. FIG. 3E shows relative β-galactosidase activity in HEK293 transfected with sensor plasmid and RNAi plasmids at different ratios. TR, terminal repeat. mTR, mutant TR. The amount of sensor plasmid and shApob plasmid for transfection was indicated.

FIG. 5A shows motifs in miRNA genes (top) and in mmu-pri-miR-33 (middle). The underlined variable nucleotides in mmu-pri-miR-33 were converted into the motifs of miRNA genes (shaded nucleotides in the bottom) to generate two modified miR-33 scaffolds. SEQ ID NOs: 78-81 are shown top to bottom. FIG. 5B shows dose response curves for knockdown efficacy in the Apob, PC-1, and SOD1 genes in HEK293 cells transfected with the shRNAmiR-33 and modified shRNAmiR-33 plasmids at the amount varying from 2 to 200 ng, together with their sensor plasmids (200 ng). Values are mean±SD. IC50 values are listed for each construct.

DETAILED DESCRIPTION

Figure 1A:
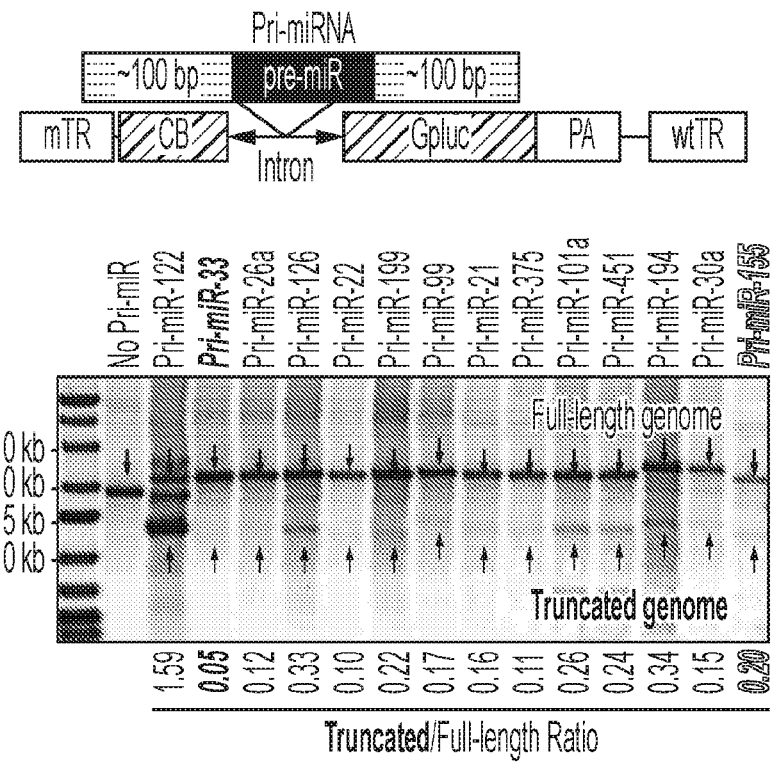
FIGS. 1A-1I show AAV compatible miRNA scaffolds for effective gene silencing in cultured cells and mice.

The disclosure relates, in some aspects, to isolated nucleic acids and recombinant Adeno-associated viruses (rAAVs) engineered to express a transgene comprising an inhibitory RNA guide strand (e.g., a guide strand targeting a human gene, such as SOD1 or PC1) inserted into an artificial miRNA scaffold (e.g., a scaffold derived from mouse miRNA-33). The disclosure is based, in part, on compositions which improve genomic integrity of rAAV vectors, and, in some embodiments, achieve a reduction in off-target gene silencing while maintaining effective gene knockdown. Accordingly, some embodiments of the disclosure relate to rAAV vectors comprising a transgene which expresses an isolated nucleic acid comprised of a mouse pri-miRNA scaffold and a guide strand that targets human gene of interest or gene transcript.

Isolated Nucleic Acids

Aspects of the disclosure relate to isolated nucleic acids encoding a transgene engineered to express one or more (e.g., 1, 2, 3, 4, 5, or more) inhibitory nucleic acids (e.g., an inhibitory RNA, such as an artificial miRNA, amiRNA). The one or more inhibitory nucleic acids may target (e.g., hybridize or specifically bind to) the same gene (e.g., hybridize or specifically bind to different sequences of the same gene) or different genes (e.g., hybridize or specifically bind to different genes).

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

In some embodiments, any one or more thymidine (T) nucleotides or uridine (U) nucleotides in a sequence provided herein may be replaced with any other nucleotide suitable for base pairing (e.g., via a Watson-Crick base pair) with an adenosine nucleotide. For example, T may be replaced with U, and U may be replaced with T.

Inhibitory nucleic acids are small, non-coding RNAs that mediate gene silencing by various mechanisms. In some embodiments, an inhibitory RNA forms a hairpin structure. Generally, hairpin-forming RNAs are arranged into a self-complementary "stem-loop" structure that includes a single nucleic acid encoding a stem portion having a duplex comprising a sense strand (e.g., passenger strand) connected to an antisense strand (e.g., guide strand) by a loop sequence. The passenger strand and the guide strand share complementarity. In some embodiments, the passenger strand and guide strand share 100% complementarity. In some embodiments, the passenger strand and guide strand share at least 50%, at least 60%, at least 70%, at least 80%, at least 90%, at least 95%, or at least 99% complementarity. A passenger strand and a guide strand may lack complementarity due to a base-pair mismatch. In some embodiments, the passenger strand and guide strand of a hairpin-forming RNA have at least 1, at least 2, at least 3, at least 4, at least 5, at least 6, at least 7 at least 8, at least 9, or at least 10 mismatches. Generally, the first 2-8 nucleotides of the stem (relative to the loop) are referred to as "seed" residues and play an important role in target recognition and binding. The first residue of the stem (relative to the loop) is referred to as the "anchor" residue. In some embodiments, hairpin-forming RNA have a mismatch at the anchor residue.

In some embodiments, an inhibitory RNA is processed in a cell (or subject) to form a "mature miRNA". Mature miRNA is the result of a multistep pathway which is initiated through the transcription of primary miRNA from its miRNA gene or intron, by RNA polymerase II or III generating the initial precursor molecule in the biological pathway resulting in miRNA. Once transcribed, pri-miRNA (often over a thousand nucleotides long with a hairpin structure) is processed by the Drosha enzyme which cleaves pri-miRNA near the junction between the hairpin structure and the ssRNA, resulting in precursor miRNA (pre-miRNA). The pre-miRNA is exported to the cytoplasm where is further reduced by Dicer enzyme at the pre-miRNA loop, resulting in duplexed miRNA strands.

Of the two strands of a miRNA duplex, one arm, the guide strand (miR), is typically found in higher concentrations and binds and associates with the Argonaute protein which is eventually loaded into the RNA-inducing silencing complex (RISC). The guide strand miRNA-RISC complex helps regulates gene expression by binding to its complementary sequence of mRNA, often in the 3' UTR of the mRNA. The non-guide strand of the miRNA duplex is known as the passenger strand and is often degraded, but may persist and also act either intact or after partial degradation to have a functional role in gene expression.

In some embodiments, a transgene is engineered to express an inhibitory nucleic acid (e.g., an miRNA) having a guide strand that targets a human gene. "Targeting" refers to hybridization or specific binding of an inhibitory nucleic acid to its cognate (e.g., complementary) sequence on a target gene (e.g., mRNA transcript of a target gene). In some embodiments, an inhibitory nucleic acid that targets a gene shares a region of complementarity with the target gene that is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides in length. In some embodiments, a region of complementarity is more than 30 nucleotides in length.

Typically, the guide strand targets a human gene associated with a disease or disorder, for example SOD1 (associated with amyotrophic lateral sclerosis, ALS) or PC1 (associated with obesity). In some embodiments, a guide strand that targets SOD1 is encoded by an isolated nucleic acid comprising the sequence set forth in SEQ ID NO: 1. In some embodiments, a guide strand that targets PC-1 is encoded by an isolated nucleic acid comprising the sequence set forth in SEQ ID NO: 2.

Further examples of human genes associated with diseases or disorders include but are not limited to HTT (Huntington's disease), APP (Alzheimer's disease), ASPA (Canavan disease), MCEP2 (Rett syndrome), DMD (muscular dystrophy), etc.

In some embodiments, the inhibitory nucleic acid is 5 to 300 bases in length (e.g., 10-30, 15-25, 19-22, 25-50, 40-90, 75-100, 90-150, 110-200, 150-250, 200-300, etc. nucleotides in length). The inhibitory nucleic acid sequence encoding a pre-miRNA or mature miRNA may be 10-50, or 5-50 bases length. In some embodiments, an inhibitory nucleic acid sequence comprising a pri-miRNA scaffold (and is at least 250, 260, 270, 280, 290, or 300 bases in length. In some embodiments, the inhibitory nucleic acid comprises or consists of a sequence of bases at least 80% or 90% complementary to, e.g., at least 5, 10, 15, 20, 25 or 30 bases of, or up to 30 or 40 bases of, a target nucleic acid (e.g., a human gene, such as SOD1 or PC1), or comprises a sequence of bases with up to 3 mismatches (e.g., up to 1, or up to 2 mismatches) over 10, 15, 20, 25 or 30 bases of a target nucleic acid (e.g., a human gene, such as SOD1 or PC1).

In some embodiments, an inhibitory nucleic acid is an artificial miRNA (amiRNA). An artificial microRNA (AmiRNA) is derived by modifying a native miRNA to replace natural targeting regions of pre-mRNA with a targeting region of interest. For example, a naturally occurring, expressed miRNA can be used as a scaffold or backbone (e.g., a pri-miRNA scaffold), with the stem sequence replaced by that of an miRNA targeting a gene of interest.

An artificial precursor microRNA (pre-amiRNA) is normally processed such that one single stable small RNA is preferentially generated.

Aspects of the disclosure relate to a nucleic acid sequence encoding a guide strand targeting a human gene that is inserted in a non-human (e.g., mouse) pri-miRNA scaffold. In some embodiments, a pri-miRNA scaffold is selected from: pri-miR-122, pri-miR-33, pri-miR-26a, pri-miR-126, pri-miR-22, pri-miR-199, pri-miR-99, pri-miR-21, pri-miR-375, pri-miR-101, pri-miR-451, pri-miR-194, pri-miR-30a, and pri-miR-155. In some embodiments, the pri-miRNA is a mouse pri-miRNA-33 scaffold. In some embodiments, the pri-miRNA scaffold flanks an inhibitory nucleic acid encoding SOD1 (e.g., as set forth in SEQ ID NO: 3). In some embodiments, the pri-miRNA scaffold flanks an inhibitory nucleic acid encoding PC1 (e.g., as set forth in SEQ ID NO: 4).

A transgene may comprise one or more promoters (e.g., 1, 2, 3, 4, 5, etc.) promoters operably linked to the nucleic acid sequence encoding an inhibitory nucleic acid. As used herein, a nucleic acid sequence (e.g., coding sequence) and regulatory sequences are said to be "operably linked" when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame.

A "promoter" refers to a DNA sequence recognized by the synthetic machinery of the cell, or introduced synthetic machinery, required to initiate the specific transcription of a gene. The phrases "operatively linked," "operatively positioned," "under control" or "under transcriptional control" means that the promoter is in the correct location and orientation in relation to the nucleic acid to control RNA polymerase initiation and expression of the gene.

Generally, a promoter can be a constitutive promoter, inducible promoter, or a tissue-specific promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an RNA pol II promoter. In some embodiments, a promoter is an RNA pol III promoter, such as U6 or H1. In some embodiments, a promoter is an RNA pol II promoter. In some embodiments, a nucleic acid encoding an inhibitory nucleic acid is operably linked to a CB6 promoter. In some embodiments, a nucleic acid sequence encoding an inhibitory nucleic acid is operably linked to a RNA pol III promoter. In some embodiments, the RNA pol III promoter is a U6 promoter.

Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: retinoschisin proximal promoter, interphotoreceptor retinoid-binding protein enhancer (RS/IRBPa), rhodopsin kinase (RK), liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (α-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid further comprises a region (e.g., a second region, a third region, a fourth region, etc.) comprising a second AAV ITR. In some embodiments, an isolated nucleic acid encoding a transgene is flanked by AAV ITRs (e.g., in the orientation 5'-ITR-transgene-ITR-3'). In some embodiments, the AAV ITRs are AAV2 ITRs. In some embodiments, at least one of the AAV ITRs is a AITR, which lacks a terminal resolution site and induces formation of a self-complementary AAV (scAAV) vector.

Vectors

Aspects of the disclosure relate to vectors comprising an isolated nucleic acid encoding a transgene comprising one or more inhibitory nucleic acids (e.g., amiRNAs). As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. In some embodiments, a vector is a viral vector, such as an rAAV vector, a lentiviral vector, an adenoviral vector, a retroviral vector, etc. Thus, the term includes cloning and expression vehicles, as well as viral vectors. In some embodiments, useful vectors are contemplated to be those vectors in which the nucleic acid segment to be transcribed is positioned under the transcriptional control of a promoter.

Isolated nucleic acids of the disclosure may be recombinant adeno-associated virus (AAV) vectors (rAAV vectors). "Recombinant AAV (rAAV) vectors" are typically composed of, at a minimum, a transgene and its regulatory sequences, and 5' and 3' AAV inverted terminal repeats (ITRs). The transgene may comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In some embodiments, an isolated nucleic acid or rAAV vector comprises one or more mutant ITRs and forms a self-complementary AAV vector. As used herein, the term "self-complementary AAV vector" (scAAV) refers to a vector containing a double-stranded vector genome generated by the absence of a terminal resolution site (TR) from one of the ITRs of the AAV. The absence of a TR prevents the initiation of replication at the vector terminus where the TR is not present. In general, scAAV vectors generate single-stranded, inverted repeat genomes, with a wild-type (wt) AAV TR at each end and a mutated TR (mTR) in the middle.

The positioning of a transgene (e.g. a nucleic acid sequence encoding one or more inhibitory nucleic acids) may vary. In some embodiments, an rAAV vector (e.g., scAAV vector) comprises inverted terminal repeats (ITRs) at each of two ends (e.g., the 5' and 3' ends of the nucleic acid sequence) and a central portion comprising a promoter operably linked with a sequence encoding an inhibitory nucleic acid. In some embodiments, the sequence encoding a inhibitory nucleic acid is substituted at a position of the self-complementary nucleic acid normally occupied by a mutant ITR.

Recombinant Adeno-Associated Viruses (rAAVs)

Aspects of the disclosure relate to recombinant adeno-associated viruses (rAAVs) comprising an inhibitory nucleic acid as described herein. In some aspects, the disclosure provides isolated adeno-associated viruses (AAVs). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s) (e.g., neurons, hepatocytes, etc.). The AAV capsid is an important element in determining these tissue-specific targeting capabilities (e.g., tissue tropism). Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein has a tropism for liver tissue (e.g., hepatocytes, etc.). In some embodiments, an AAV capsid protein does not target neuronal cells. In some embodiments, an AAV capsid protein does not cross the blood-brain barrier (BBB). In some embodiments, an AAV capsid is capable of crossing the BBB and/or specifically (or preferentially) targets CNS cells, such as neuronal cells or glial cells.

In some embodiments, an AAV capsid protein is of an AAV serotype selected from the group consisting of AAV1, AAV2, AAV3, AAV4, AAV5, AAV6, AAV7, AAV8, AAV9, AAV9.hr, AAVrh8, AAVrh10, AAVrh39, AAVrh43, AAV.PHP.B, AAV.PHP.eB, and variants of any of the foregoing. In some embodiments, an AAV capsid protein is of a serotype derived from a non-human primate, for example AAVrh8 serotype.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the disclosure relates to a host cell containing a nucleic acid that comprises a transgene engineered to express one or more inhibitory nucleic acids as described herein. A "host cell" refers to any cell that harbors, or is capable of harboring, a substance of interest. Often a host cell is a mammalian cell. In some embodiments, a host cell is a neuron. In some embodiments, a host cell is a hepatocyte. In some embodiments, a host cell is a kidney cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. In some embodiments, the host cell is a mammalian cell, a yeast cell, a bacterial cell, an insect cell, a plant cell, or a fungal cell. In some embodiments, the host cell is a hepatocyte.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an AAV vector (comprising a transgene flanked by ITR elements) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpes virus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

Pharmaceutical Compositions

The isolated nucleic acids and rAAVs of the disclosure may be delivered to a subject in compositions according to any appropriate methods known in the art. For example, an rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intracerebroventricular, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{12}$ or $10^{13}$ rAAV genome copies is effective to target CNS tissue. In some cases, stable transgenic animals are produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Methods

In some aspects, inhibitory nucleic acids described herein are useful for inhibiting (e.g., reducing or silencing) expression of a target gene (e.g., mRNA transcript of a target gene) in a cell or subject. A "target gene" generally refers to a gene the expression of which it is desirable to inhibit. In some embodiments, a target gene expresses a mutant protein or protein associated with a disease or disorder. In some embodiments, the target gene is a gene associated with a neurodegenerative disease (e.g., ALS, Huntington's disease, Canavan disease, Alzheimer's disease, etc.). In some embodiments, the target gene is SOD1. In some embodiments, the target gene is a gene associated with obesity, for example PC1.

In some embodiments, administration of isolated nucleic acids and rAAVs described herein to a cell or subject results in inhibition of target gene expression in the cell or subject (e.g., inhibition relative to the level of target gene expression prior to the administration, or relative to a healthy control subject). In some embodiments, administration results in inhibition of target gene expression of at least 2-fold, 3-fold, 4-fold, 5-fold, 10-fold, 50-fold, 100-fold, or 1000-fold. In some embodiments, administration results in inhibition of target gene expression more than 1000-fold. In some embodiments, administration results in inhibition of target gene expression of at least 50%, 60%, 70%, 80%, 90%, 95%, or 99%. In some embodiments, administration results in complete (e.g., 100%, or no expression) inhibition of target gene expression.

Methods for delivering a transgene (e.g., an isolated nucleic acid or rAAV engineered to express one or more inhibitory nucleic acids as described herein) to a cell or a subject are provided by the disclosure. The methods typically involve administering to a subject an effective amount of an isolated nucleic acid encoding the transgene(s). In some embodiments, expression constructs described by the disclosure are useful for treating diseases, such as ALS or obesity.

In some aspects the disclosure relates to a method of treating amyotrophic lateral sclerosis (ALS) in a subject, the method comprising administering to a subject in need thereof an effective amount of an isolated nucleic acid or an rAAV as described herein. A subject may be any mammalian organism, for example a human, non-human primate, horse, pig, dog, cat rodent, etc. In some embodiments a subject is a human.

In some aspects the disclosure relates to a method of treating obesity in a subject, the method comprising administering to a subject in need thereof an effective amount of an isolated nucleic acid or an rAAV as described herein. A subject may be any mammalian organism, for example a human, non-human primate, horse, pig, dog, cat rodent, etc. In some embodiments a subject is a human.

An "effective amount" of a substance is an amount sufficient to produce a desired effect. In some embodiments, an effective amount of an isolated nucleic acid is an amount sufficient to transfect (or infect in the context of rAAV mediated delivery) a sufficient number of target cells of a target tissue of a subject. In some embodiments, a target tissue is liver tissue (e.g., hepatocytes, neurons, etc.). In some embodiments, an effective amount of an isolated nucleic acid (e.g., which may be delivered via an rAAV) may be an amount sufficient to have a therapeutic benefit in a subject, e.g., to decrease the expression of one or more genes associated with ALS (e.g., SOD1) or obesity (e.g., PC1), to extend the lifespan of a subject, to improve in the subject one or more symptoms of disease (e.g., a symptom of ALS or obesity), etc. The effective amount will depend on a variety of factors such as, for example, the species, age, weight, health of the subject, and the tissue to be targeted, and may thus vary among subject and tissue as described elsewhere in the disclosure.

In some embodiments, the term "treating" refers to the application or administration of a composition encoding a transgene(s) to a subject, who has ALS, a symptom of ALS, or a predisposition toward ALS (e.g., one or more mutations in a SOD1 gene, etc.), with the purpose to cure, heal, alleviate, relieve, alter, remedy, ameliorate, improve, or affect the disorder, the symptom of the disease, or the predisposition toward ALS.

In some embodiments, the term "treating" refers to the application or administration of a composition encoding a transgene(s) to a subject, who has obesity, a symptom of obesity, or a predisposition toward obesity (e.g., one or more mutations in a PC1 gene, etc.), with the purpose to cure, heal, alleviate, relieve, alter, remedy, ameliorate, improve, or affect the disorder, the symptom of the disease, or the predisposition toward obesity.

Alleviating disease (e.g., ALS or obesity) includes delaying the development or progression of the disease, or reducing disease severity. Alleviating the disease does not necessarily require curative results. As used therein, "delaying" the development of a disease (such as ALS) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of ALS or obesity includes initial onset and/or recurrence.

In some embodiments, administration occurs via systemic injection or direct injection to the liver. In some embodiments, systemic injection is intravenous injection. In some embodiments, direct injection is intraparenchymal injection, intrahepatic injection (e.g., hepatic portal vein injection, etc.).

Kits

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for constructing an AAV vector as described herein. In addition, kits of the disclosure may include, instructions, a negative and/or positive control, containers, diluents and buffers for the sample, sample preparation tubes and a printed or electronic table of reference AAV sequence for sequence comparisons.

Exemplary embodiments of the invention are described in more detail by the following examples. These embodiments are exemplary of the invention, which one skilled in the art will recognize is not limited to the exemplary embodiments.

EXAMPLE

It has been observed that shRNA-encoded sequences redirect rAAV viral genome replication, generating truncated rAAV genomes lacking an intact shRNA cassette. The discovery of undesirable truncations caused by hairpin sequences in rAAV genomes highlights the importance of developing AAV-compatible gene silencing vectors with a high proportion of intact genomes.

Figure 3A:
FIGS. 3A-3E show thermodynamic stability of the DNA encoding shRNAs influences rAAV genome homogeneity.
Figure 3B:
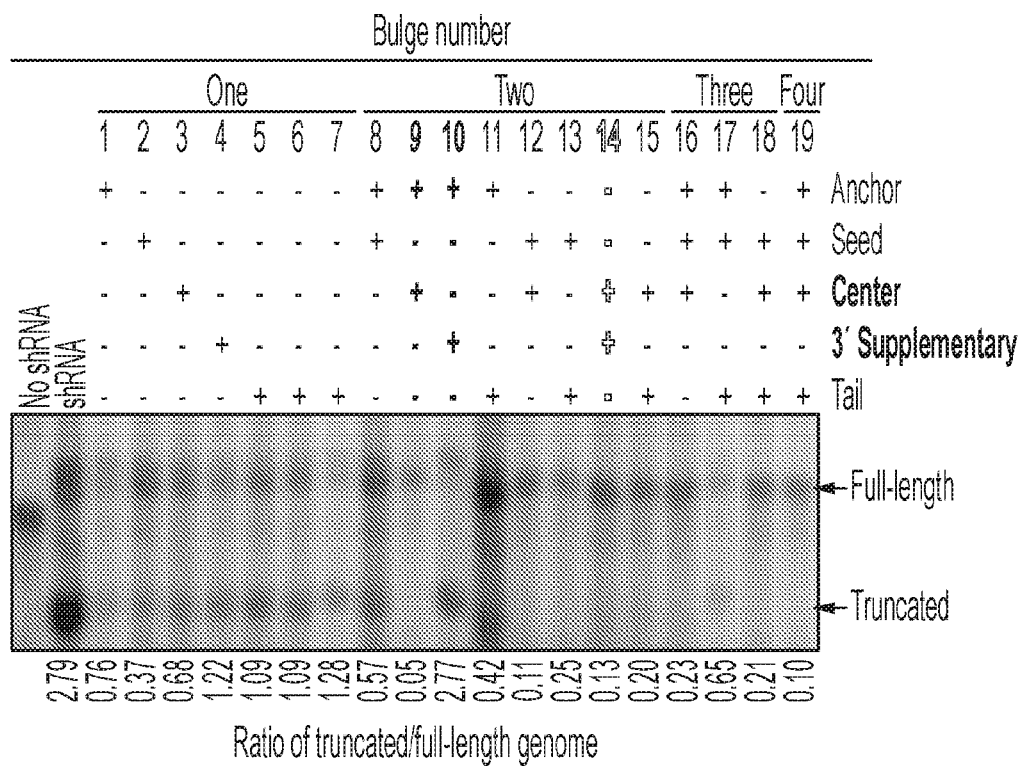
Figure 3C:
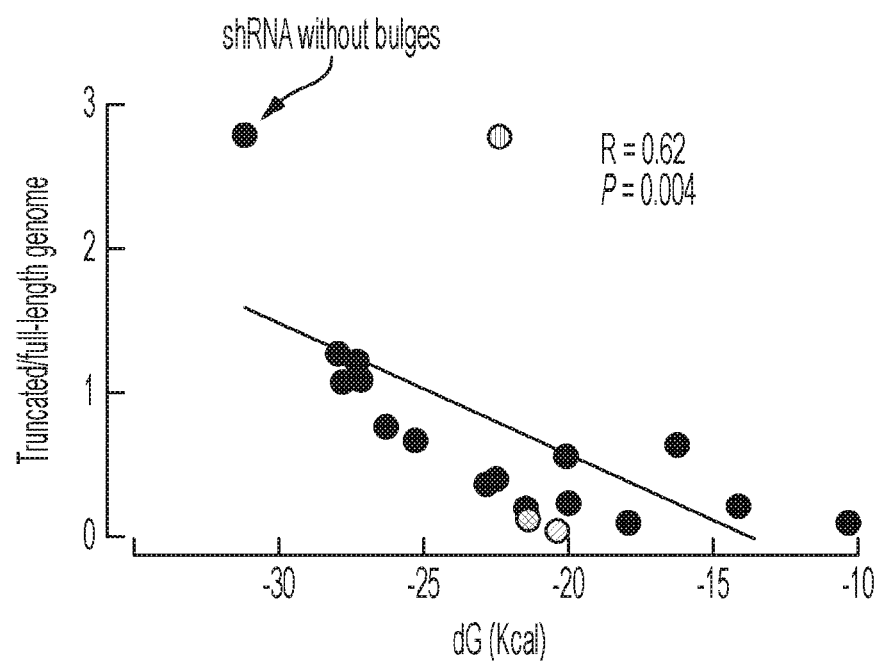
Figure 3D:
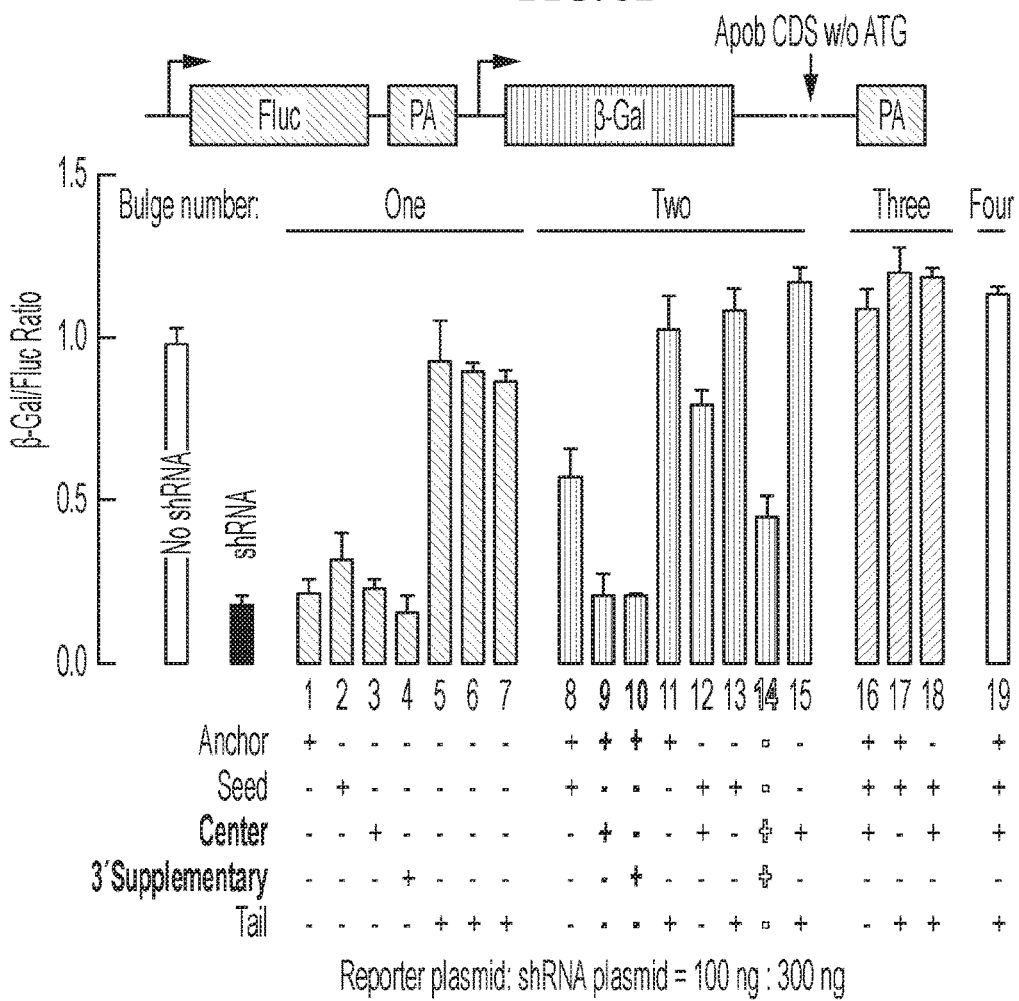
Figure 3E:
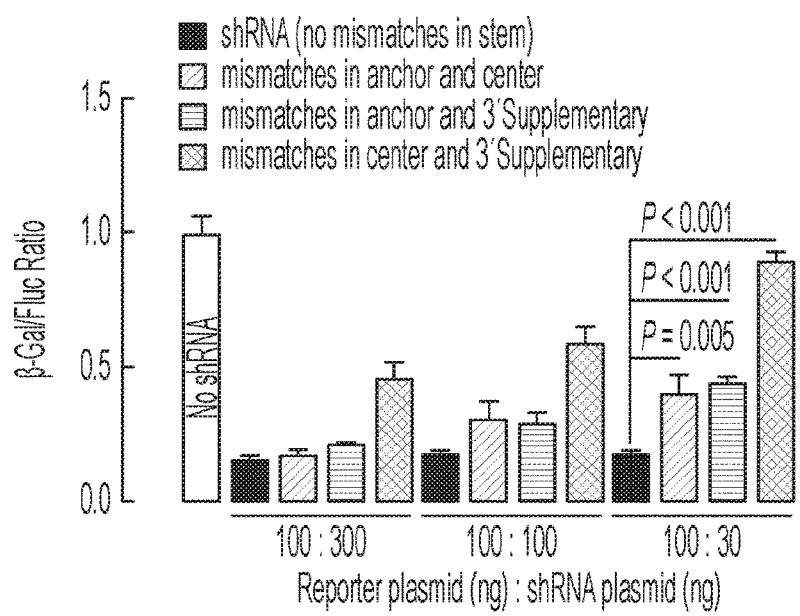
Figure 4:
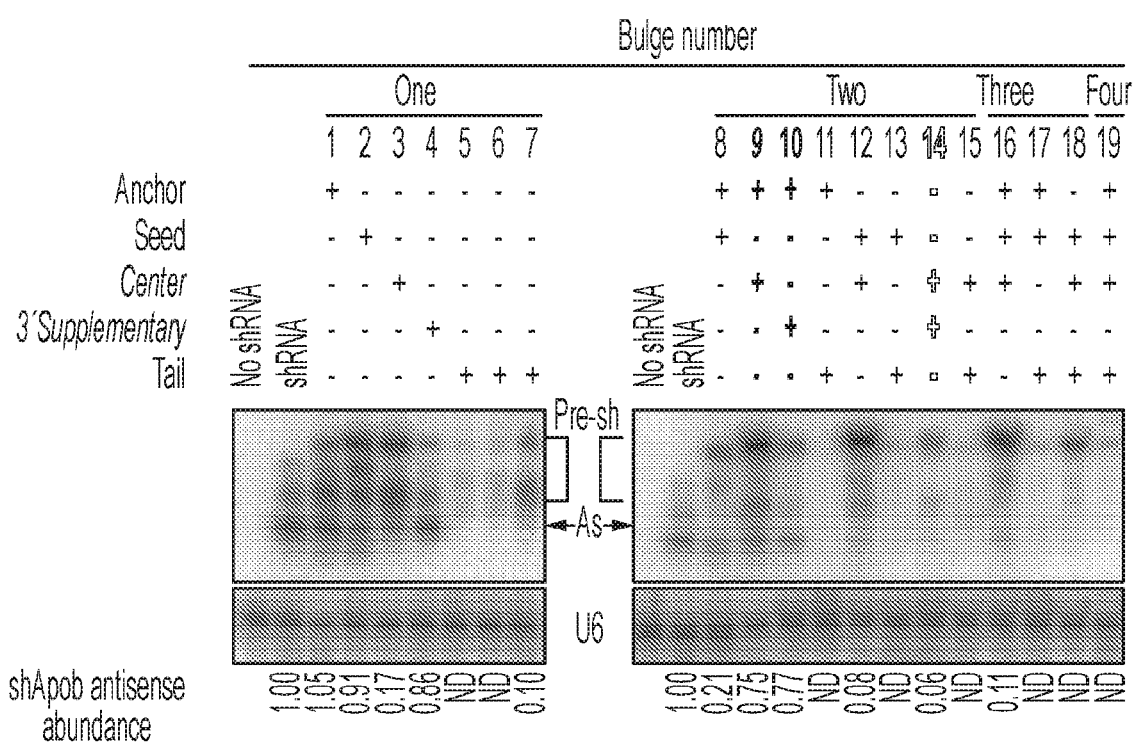
FIG. 4 shows a small RNA Northern blot analysis of shApob antisense levels in HEK293 cells transfected with the shApob constructs with/without bulge.

The question of whether introducing mismatches into the shRNA stem improves rAAV genome integrity was investigated. Up to four dinucleotide mismatches were introduced at different positions in an shDNA passenger strand, without changing the guide strand (FIG. 3A). Lowering the thermodynamic stability of the shDNA sequence improved rAAV genome integrity (FIGS. 3B-3C), but at the cost of reduced RNAi efficacy (FIGS. 3D-3E). An abundance of unprocessed precursors and less functional antisense small RNA (FIG. 4) were observed.

Figure 1B:
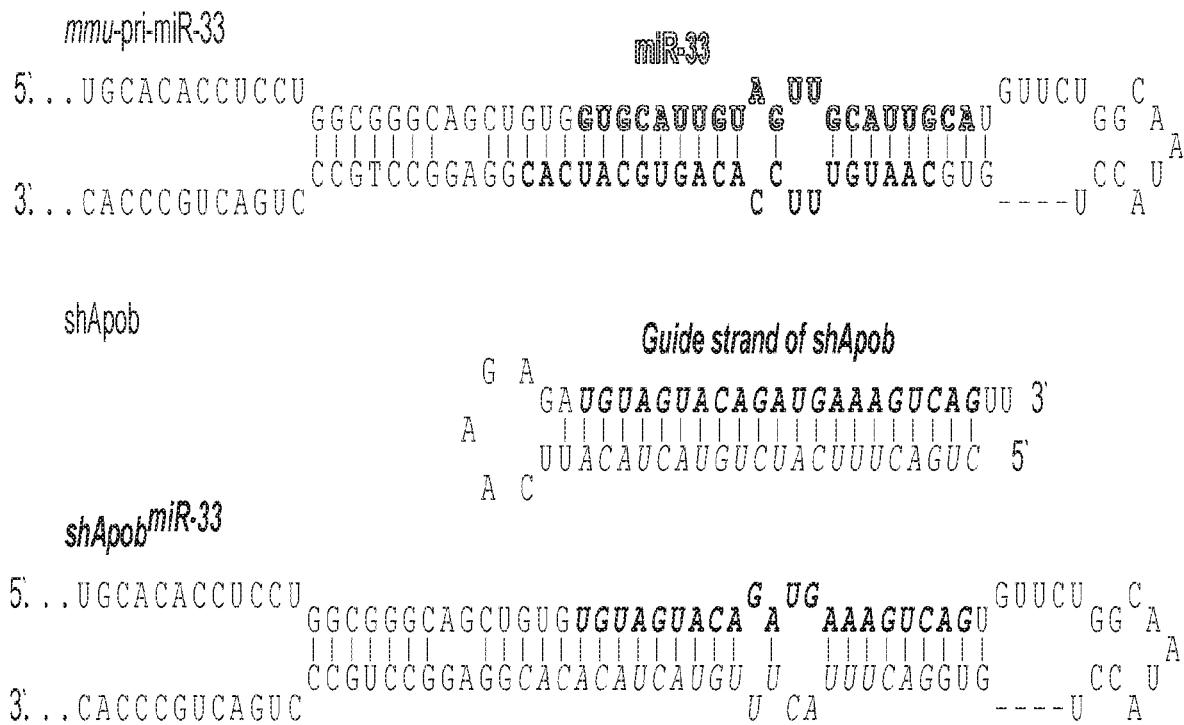

Next, whether natural pre-miRNA scaffolds could improve rAAV genome integrity without compromising efficacy was tested. rAAV constructs harboring DNA sequences originated from 15 different mouse primary miRNAs (pri-miRNAs), the transcripts that undergo sequential processing into pre-miRNAs then into miRNAs, were produced and packaged into AAV capsids. Agarose gel analysis of viral DNA showed that the frequency of genome truncation varied among the pri-miRNAs tested (FIG. 1A). Candidates that generated the least truncation were selected for use as scaffolds in which the Apolipoprotein B (Apob) antisense sequence was embedded. Specifically, artificial miRNA scaffolds (named shRNAmiRNA hereafter) were produced by replacing the original miRNA guide strands with the shApob guide strand, while incorporating bulges into the passenger strands that mimic the native structures of the corresponding endogenous miRNAs. Additionally, the pre-miRNA loop and the flanking sequences (~100 bases) were derived from the corresponding endogenous mouse pri-miRNAs. FIG. 1B shows an example of a mmu-pri-miR-33 construct.

Figure 5A:
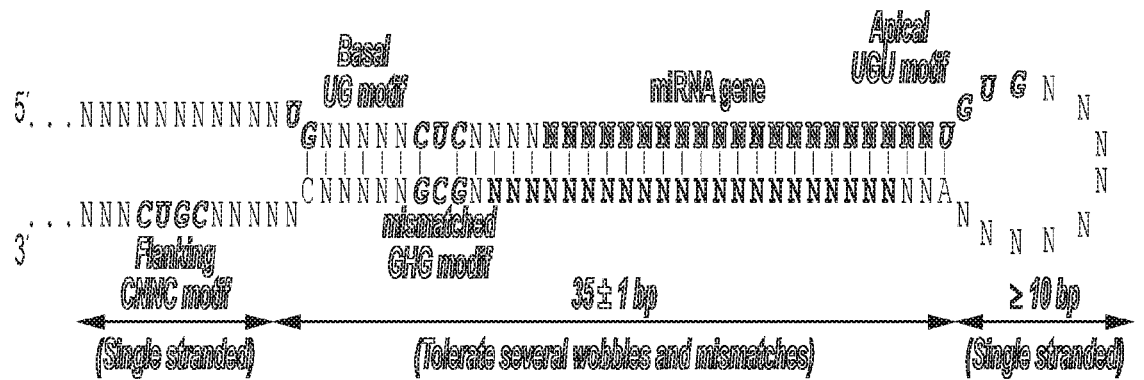
FIGS. 5A-5B show feature motifs of miRNA genes in the pri-mmu-miR-33 scaffold.
Figure 5A:
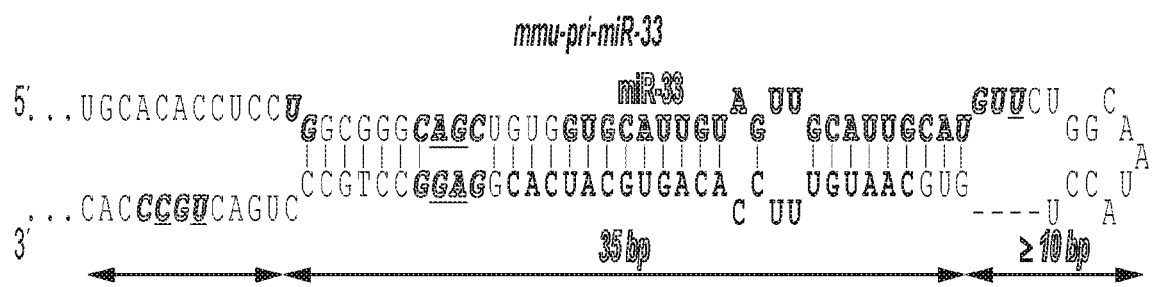
Figure 5A:
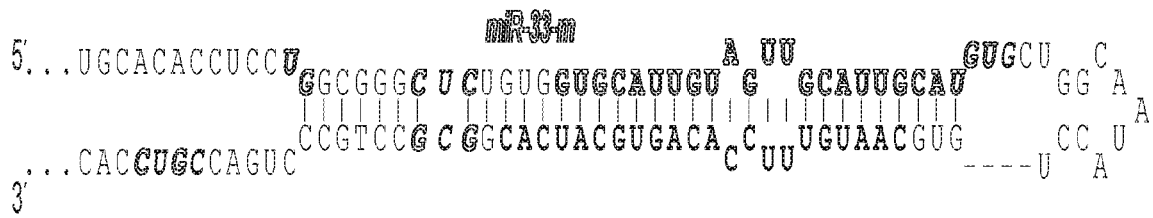
Figure 5A:
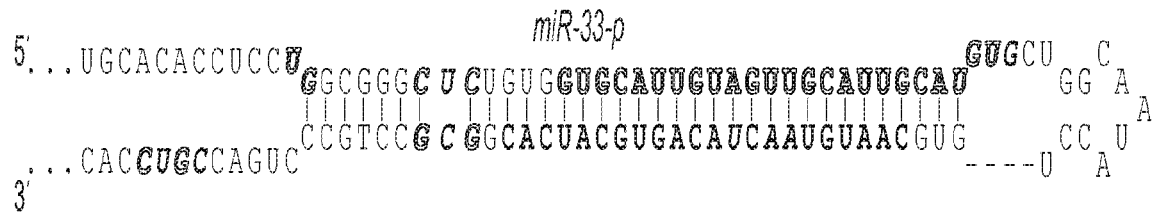
Figure 5B:
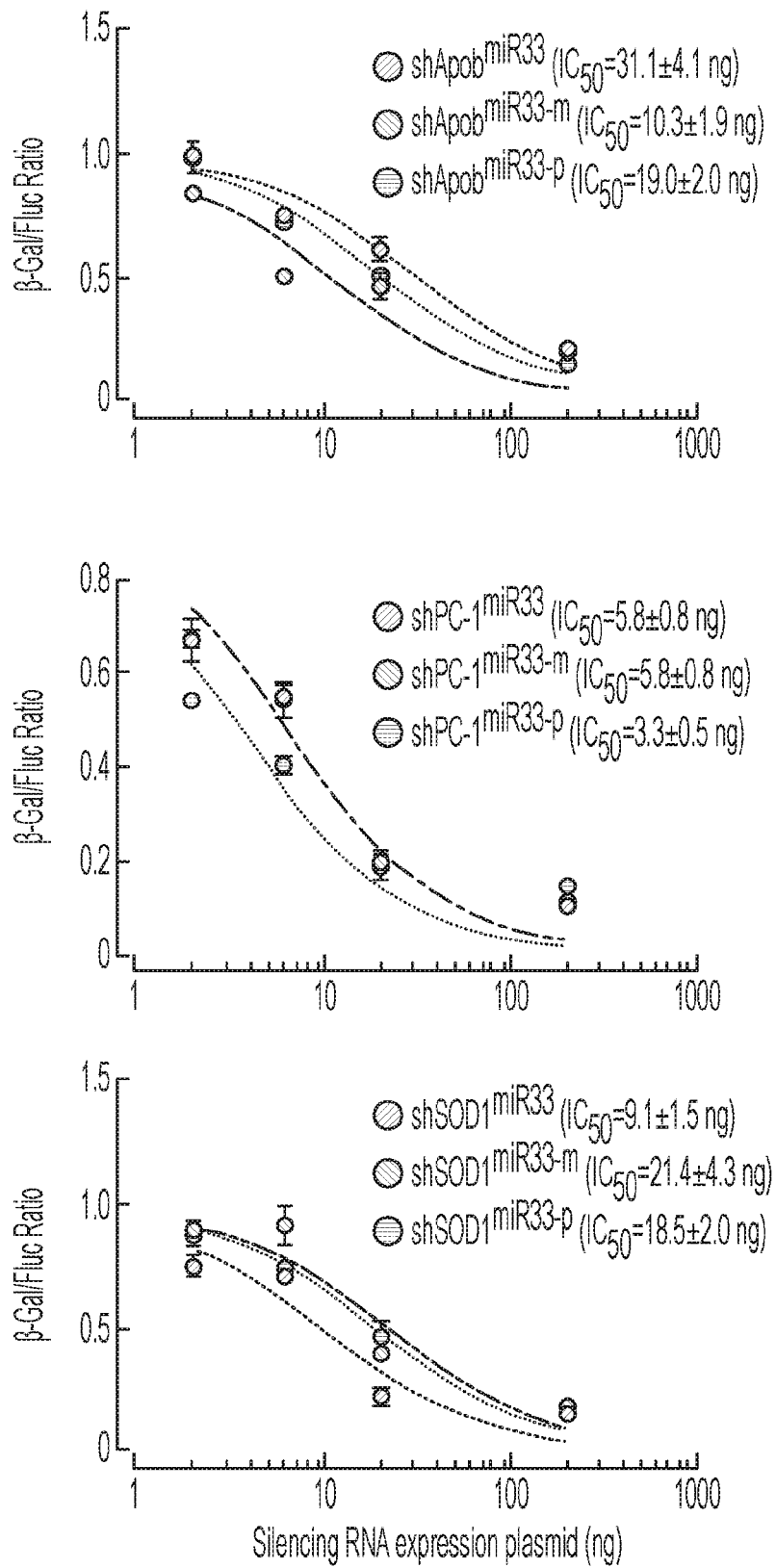

The mmu-pri-miR-33 transcript contains nearly all features of an optimal miRNA including a 35-basepair stem, a UG motif at the 5' end of the pre-miRNA, a mismatched GHG motif in the stem, a UGUG motif in the loop, a CNNC motif downstream of the pre-miRNA 3' end (FIG. 5A). The sub-optimal nucleotides in mmu-pri-miR-33 were converted into the exact motifs of De Novo designed miRNA genes to generate two additional scaffolds, miR-33-m and miR-33-p (FIG. 5A, bottom). miR-33-m possesses a bulged-stem like endogenous miR-33, whereas miR-33-p carries a perfectly complementary stem. Dose-response analyses showed that the modified miR-33 scaffolds were more efficient knockdown of Apob (FIG. 5B, top), comparable to the parent construct for PC-1 (FIG. 5B, middle), and less efficient for SOD1 (FIG. 5B, bottom). Overall, the introduction of optimal miRNA motifs failed to further enhance the potency of the miR-33 scaffold.

Figure 1C:
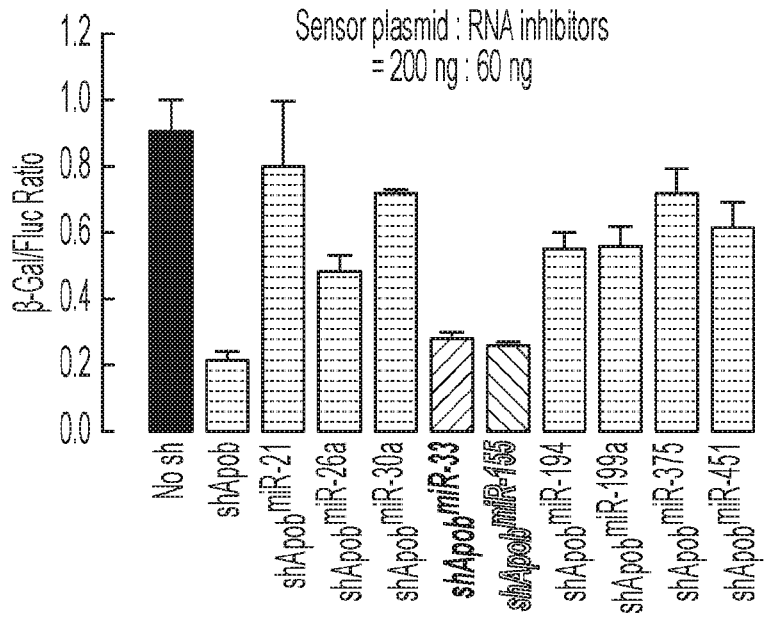
Figure 1D:
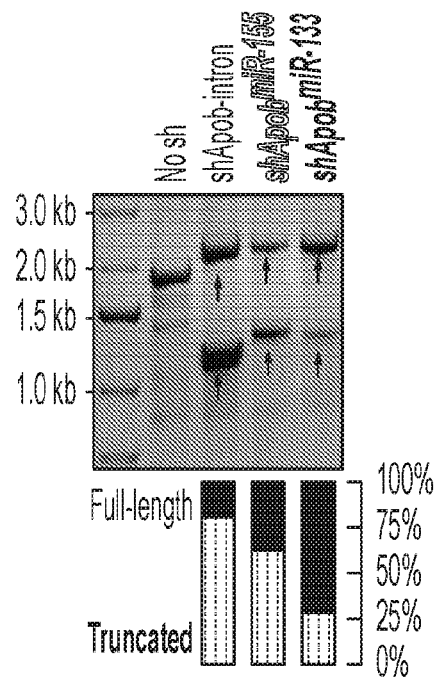

RNAi potency was measured for conventional shApob- and shApobmiRNA-expressing plasmids in HEK293 cells. Driving shRNAmiR-33 and shRNAmiR-155 transcription by a CMV enhancer/chicken β-actin (CB) Pol II promoter achieved reductions of reporter gene expression comparable to the silence produced by an H1 promoter Pol III-driven conventional shRNA (FIG. 1C). Each of the shRNAmiR-expressing vector genomes was packaged into an rAAV and the genome integrity of viral DNA extracted from purified vectors was examined. The miR-33 (shApobmiR-33) and miR-155 (shApobmiR-155) scaffolds yielded ~25% and ~60% truncated genomes, respectively, compared to ~80% for shApob (FIG. 1D).

Figure 1E:
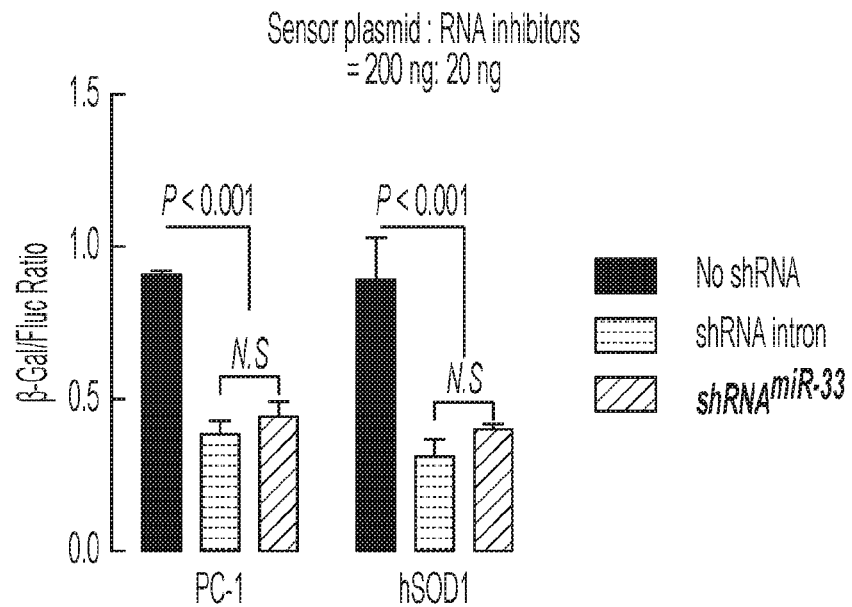
Figure 1F:
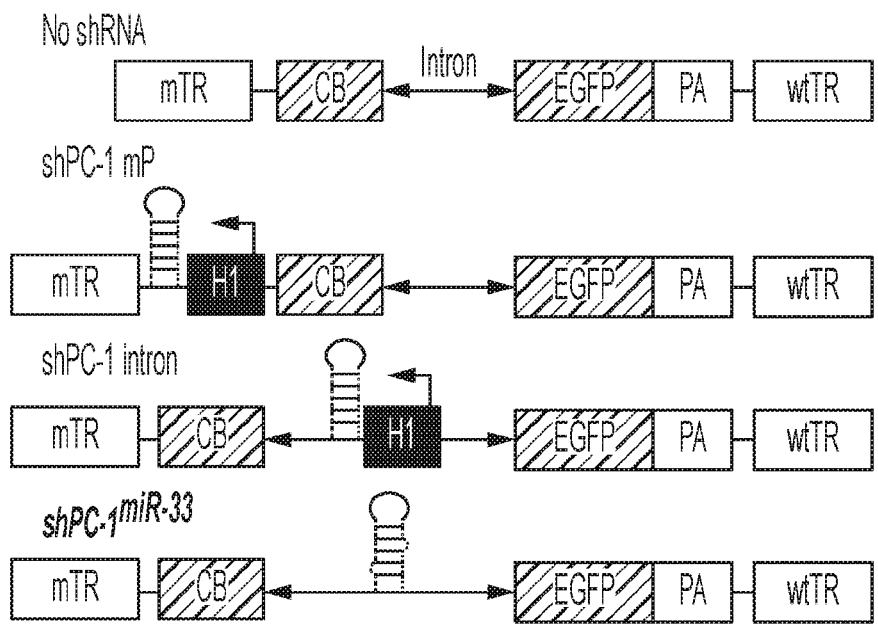
Figure 1G:
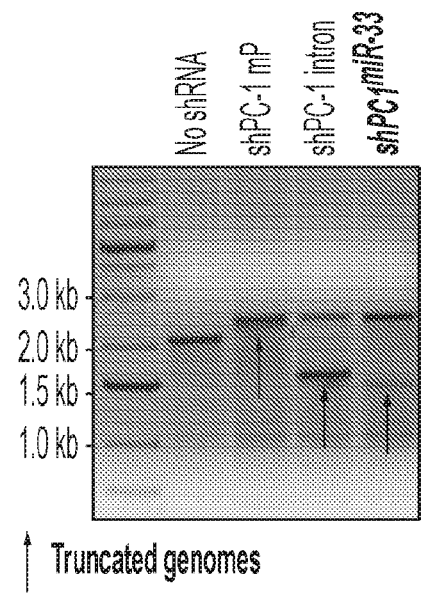
Figure 1H:
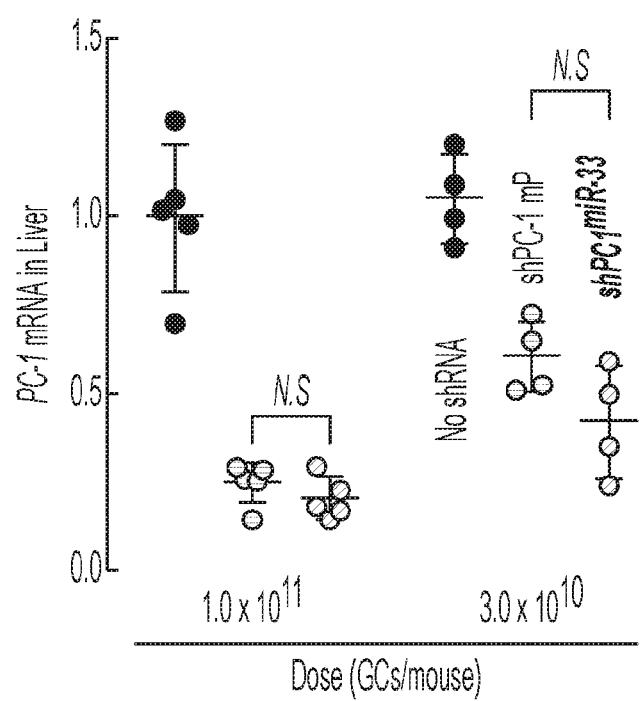
Figure 1I:
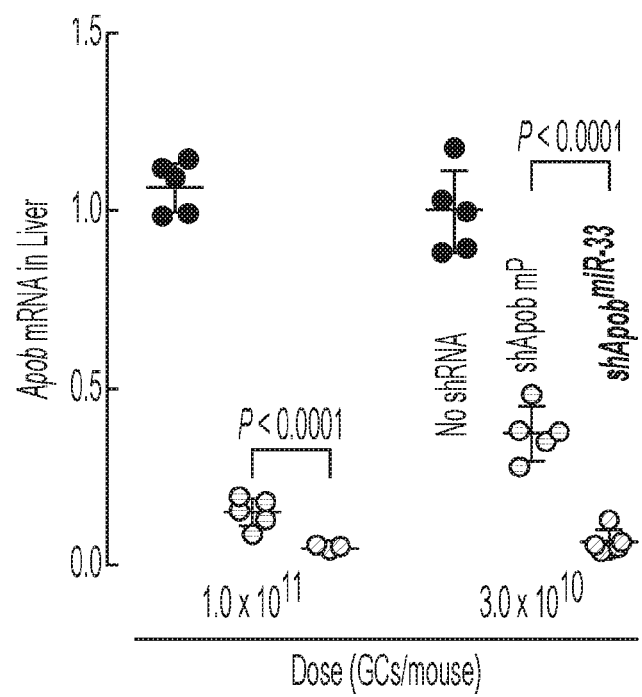

To test if the miR-33 scaffold is a versatile gene knockdown platform, shRNAmiR-33 vectors targeting Proprotein convertase 1 (PC-1) and Superoxide dismutase 1 (SOD1) were produced. In HEK293 cells, the knockdown efficacy of these shRNAmiR-33 constructs was as potent as an shRNA driven by a strong Pol III H1 promoter (FIG. 1E). Constructs harboring shPC-1miR-33 (within the intron), or shPC-1 (next to the mutant terminal repeat or within the intron) were packaged into AAV capsids (FIG. 1F). We positioned the shPC-1 next to the mutant terminal repeat to decrease the proportion of truncated genomes (FIG. 1G, shPC-1-mp in lane 3). The vectors were administered intravenously to adult mice. After three weeks, liver PC-1 or Apob mRNA levels were measured using quantitative reverse transcription-PCR (FIGS. 1H-1I). Compared to AAV-shRNA vectors, shRNAmiR-33 achieved comparable gene knockdown of PC-1 mRNA and more efficient down-regulation of Apob mRNA in mice (FIGS. 1H-1I). Taken together, data indicate that the miR-33 scaffold improves rAAV genome integrity and achieves effective gene silencing in cultured cells and mice.

Figure 2A:
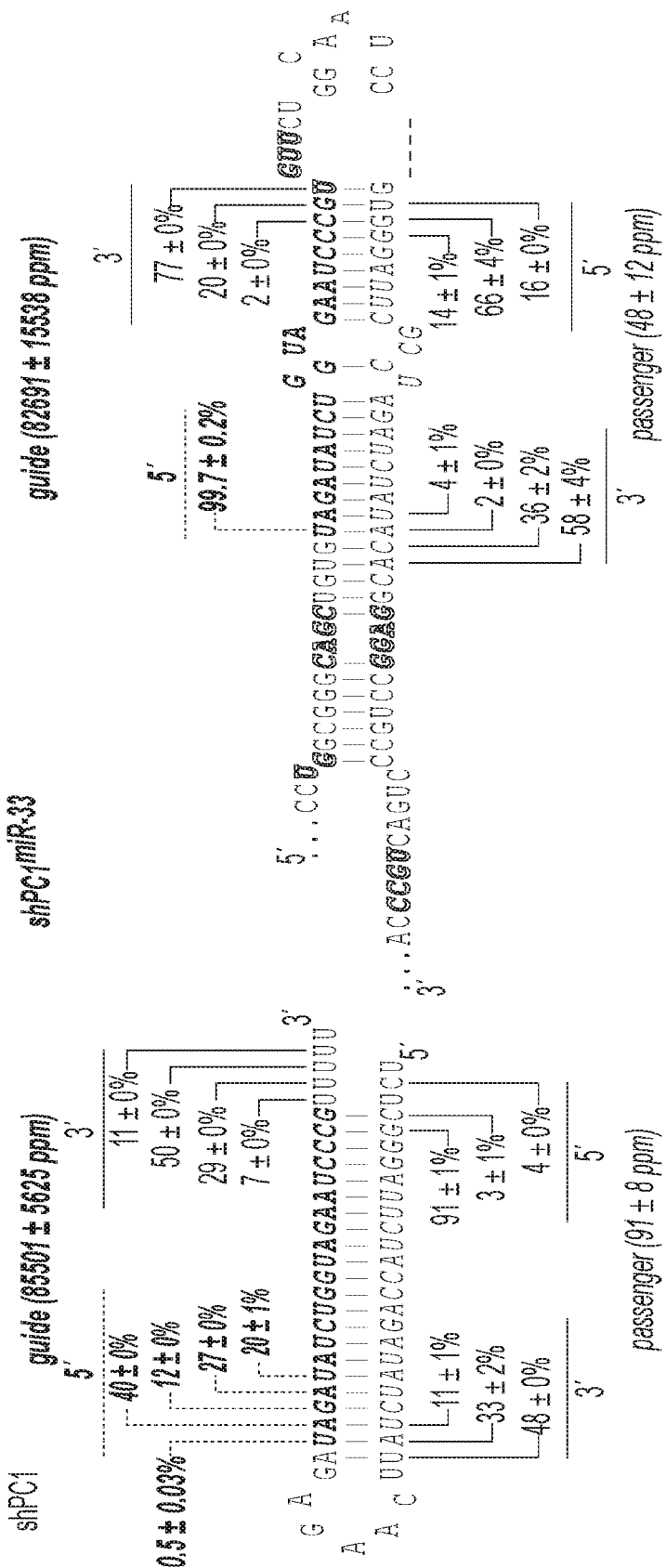

Small RNAs and mRNAs were quantified from liver RNA extracted from mice receiving $1.0 \times 10^{11}$ genome copies three weeks after tail vein injection (FIG. 1H). These data indicated that both the conventional shRNA and the shRNAmiR-33 scaffold promoted efficient loading of their guide strand into Argonaute: passenger strands were <0.1% of small RNAs generated for shPC-1 (guide strand, $85\pm6\times10^3$ ppm; passenger strand, $91\pm8$ ppm) or shPC-1miR-33 (guide strand, $83\pm16\times10^3$ ppm; passenger strand, $48\pm12$ ppm) treated mice. However, the 5' ends of the shPC-1-derived guide strands were highly heterogeneous. Majority of the 5' ends were shifted one to four nucleotides to 3' for AAV-shPC-1, producing four different seeds and 99.5±0.03% of which were not the intended sequence. 0.3±0.2% incorrect 5' ends were detected among >2.2±0.4 million guide strand reads for shPC-1miR-33. Thus, shPC-1miR-33 generated as a single seed sequence (FIG. 2A).

Figure 2B:
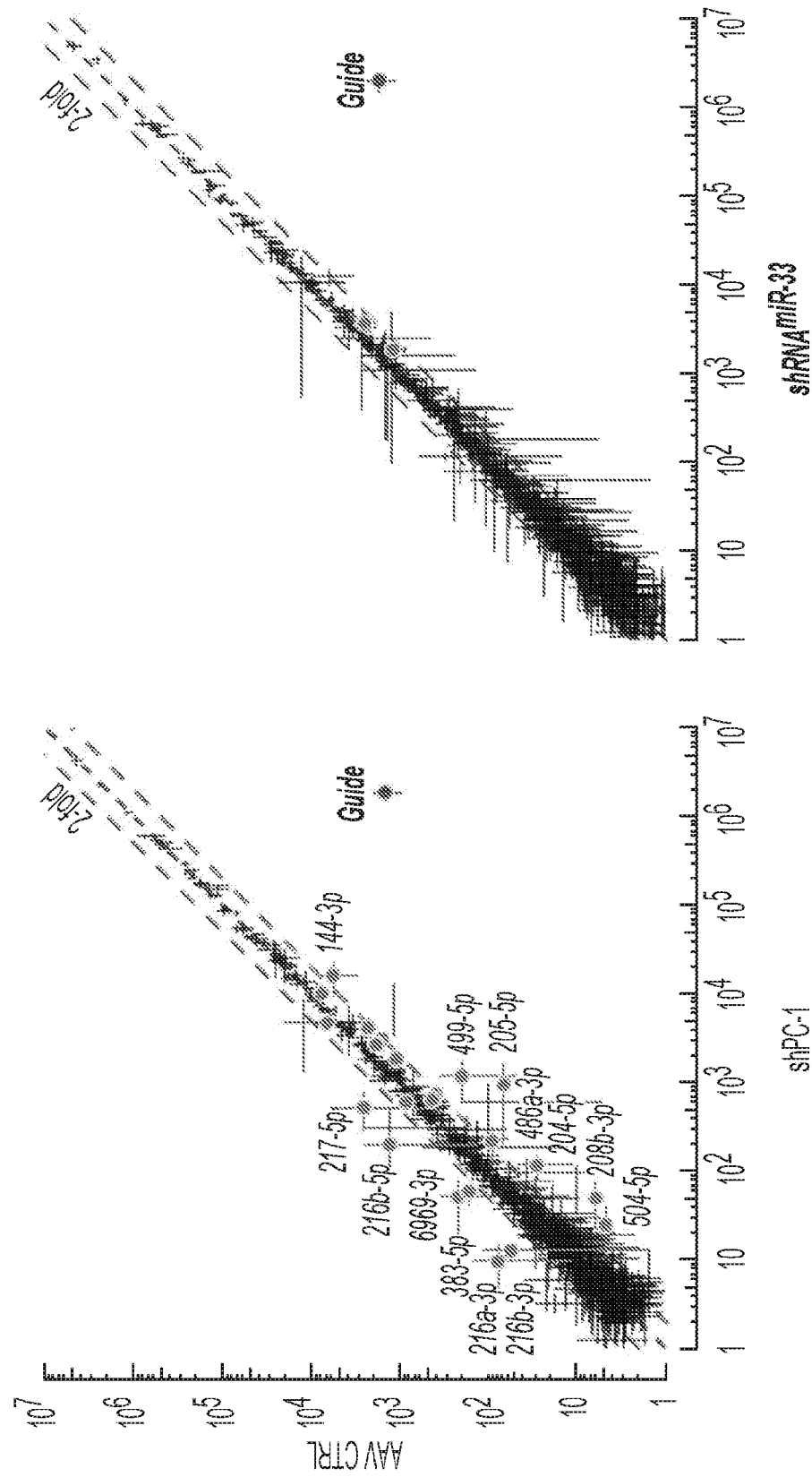
Figure 6:
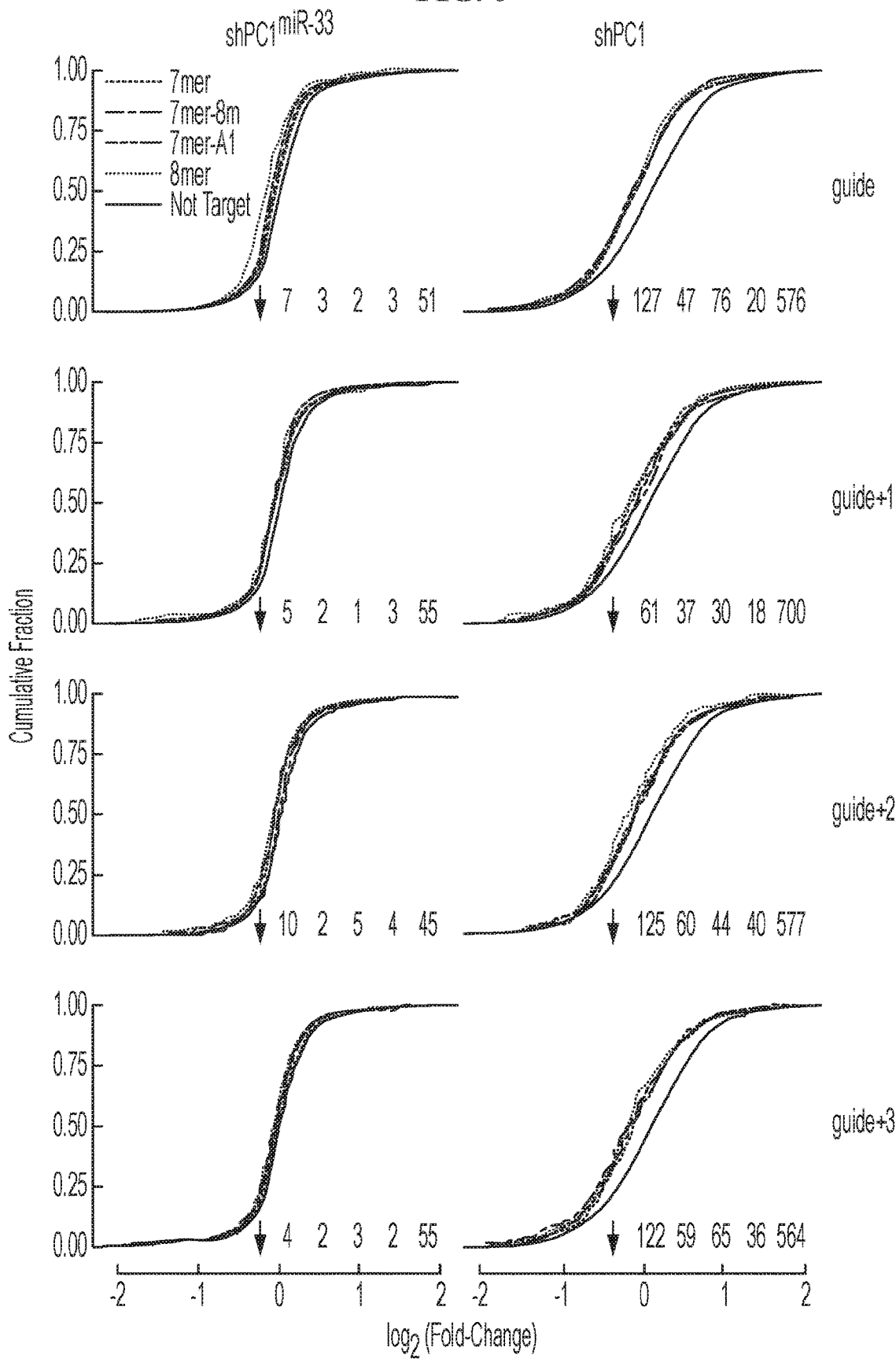
FIG. 6 shows imprecise processing of shRNA causes off-target knockdown. Gene-coding mRNAs are categorized based on difference pairing of their 3' UTR sequences to difference guide isoforms. The accumulative distribution of log 2 fold-change compared to control is plotted. Guide+1: guide isoform who 5' end has shifted 1 nucleotide towards the 3' end.

Moreover, shPC-1 perturbed endogenous miRNA levels: small RNA profiling of livers treated with AAV-shPC-1 detected 13 dysregulated miRNAs (>2-fold change and FDR <0.05); no significant changes in miRNA expression were observed in livers receiving AAV-shPC-1miR-33 (FIG. 2B). RNA-seq experiments gave similar results for mRNA expression. Compared to an AAV vector lacking a shRNA cassette, the AAV-shPC-1 vector perturbed expression of 2,547 genes (FDR <0.05; 1,221 decreased and 1,326 increased). The mRNAs whose expression decreased tended to contain seed matches to the multiple small RNA sequences generated byshPC-1 (FIG. 6).

Figure 2C:
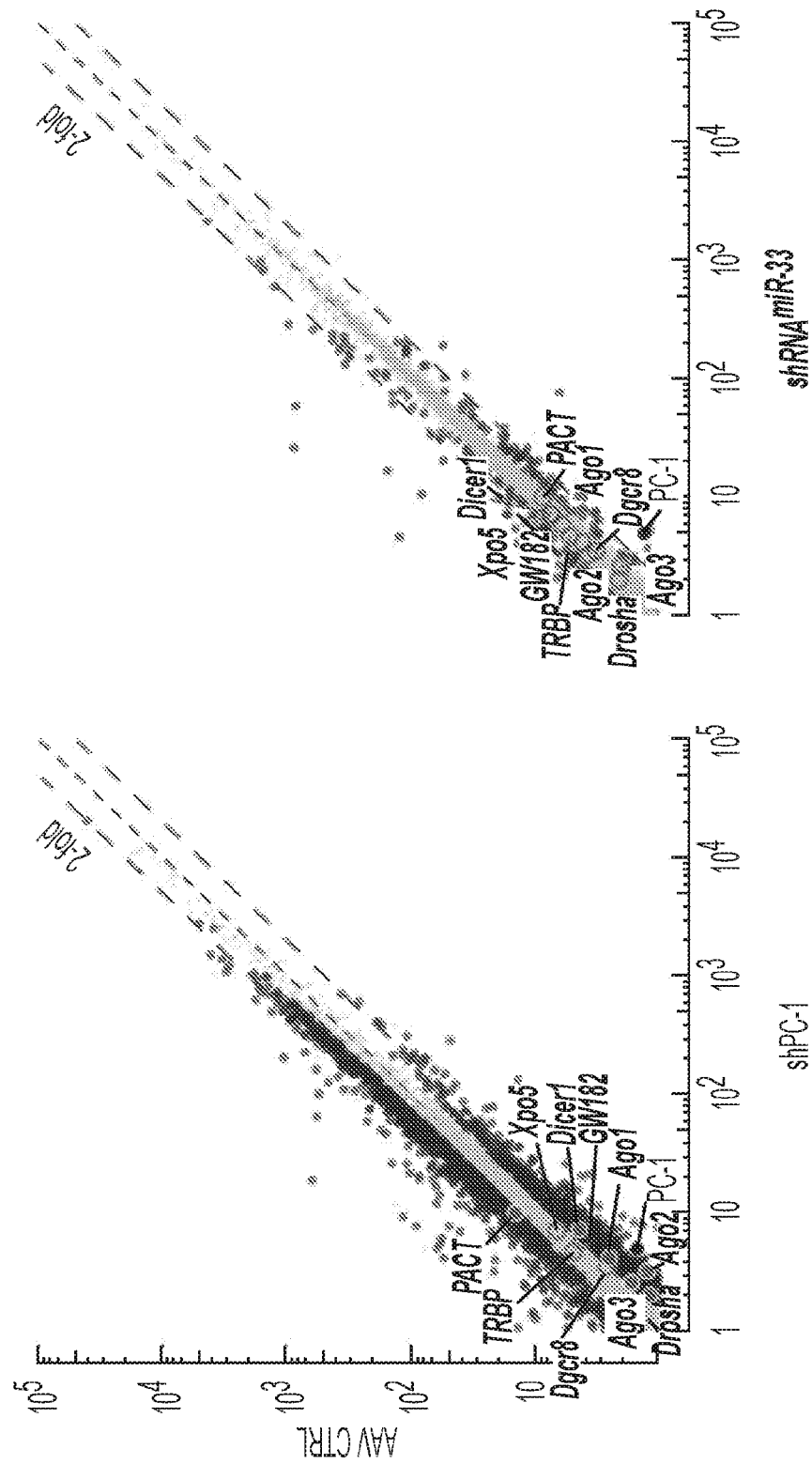

In contrast, injection of AAV-shPC-1miR-33 decreased expression of 94- and increased expression of 286 genes. shPC-1, but not shPC-1miR-33, showed alterations in mRNAs encoding RNAi pathway proteins (Ago1, Ago2, Ago3, Dicer1, Drosha, and PACT; FIG. 2C). rAAV-shRNAmiR-33 vectors showed fewer changes in global miRNA and mRNA levels than rAAV-shRNA vectors. The disturbance of global liver gene expression (FIG. 2D) by AAV-shRNA may reflect interference with the RNAi pathway or the off-targeting effect from its guide strands heterogeneous 5'ends. As a Pol II construct, shRNAmiR-33 can be transcribed from inducible or tissue- or cell-type specific promoters. Several miRNA scaffolds have been reported previously for effective and safe gene silencing, including miR-3013, miR-1557, 12 and miR-22311. Compared to previous reported miRNA scaffolds7, 11-13, miR-33 scaffold produced the most precisely processed guide strand and the least amount of passenger strand.

TABLE 1

Sequences

| Oligonucleotides | Sequences (5' to 3') | Purpose |
|---|---|---|
| pri-miR-122 F | ATCGGGCCCGACTGCAGTTTCAGCGTTTG (SEQ ID NO: 5) | To PCR mmu-pri-miR-122 |
| pri-miR-122 R | CGCGGGCCCGACTTTACATTACACACAAT (SEQ ID NO: 6) | To PCR mmu-pri-miR-122 |
| pri-miR-33 F | AGGGCTCTGCGTTTGCTCCAGG (SEQ ID NO: 7) | To PCR mmu-pri-miR-33 |
| pri-miR-33 R | AGGGTGACACTGTCCTTATT (SEQ ID NO: 8) | To PCR mmu-pri-miR-33 |
| pri-miR-26a F | GCCCCTTCTCTTTGGCAG (SEQ ID NO: 9) | To PCR mmu-pri-miR-26a |
| pri-miR-26a R | TTGGCCAGCAAGCTTGG (SEQ ID NO: 10) | To PCR mmu-pri-miR-26a |
| pri-miR-126 F | GGAAGGCATTGTGGGCGTAA (SEQ ID NO: 11) | To PCR mmu-pri-miR-126 |
| pri-miR-126 R | TGCAAAGTCTCTGGCTGTC (SEQ ID NO: 12) | To PCR mmu-pri-miR-126 |
| pri-miR-22 F | ATTTCAGGTCGTCCCATATGTC (SEQ ID NO: 13) | To PCR mmu-pri-miR-22 |

TABLE 1-continued

Sequences

| Oligonucleotides | Sequences (5' to 3') | Purpose |
| --- | --- | --- |
| pri-miR-22 R | GTCCCTCACCTTCCGGATGATAG (SEQ ID NO: 14) | To PCR mmu-pri-miR-22 |
| pri-miR-199 F | CTCAGTCCTGGGCCTACTTTTTCCA (SEQ ID NO: 15) | To PCR mmu-pri-miR-199 |
| pri-miR-199 R | TGCCACGTCAGAAGAGTTCAG (SEQ ID NO: 16) | To PCR mmu-pri-miR-199 |
| pri-miR-99 F | GGATTCCCAGCCTTTAAAATATTTAC (SEQ ID NO: 17) | To PCR mmu-pri-miR-99 |
| pri-miR-99 R | GGATTAAAAGATCCATGAAG (SEQ ID NO: 18) | To PCR mmu-pri-miR-99 |
| pri-miR-21 F | GATATCGACTGTTGGCATTAAGCCCC (SEQ ID NO: 19) | To PCR mmu-pri-miR-21 |
| pri-miR-21 R | GACTTTCCAAGTCTCACAAG (SEQ ID NO: 20) | To PCR mmu-pri-miR-21 |
| pri-miR-375 F | ACCGCGGTGCTCAGGTGAGAG (SEQ ID NO: 21) | To PCR mmu-pri-miR-375 |
| pri-miR-375 R | CAGAGACTGAGCACGGT (SEQ ID NO: 22) | To PCR mmu-pri-miR-375 |
| pri-miR-101 F | TTTTGCCTCCATCCAGAAGTGC (SEQ ID NO: 23) | To PCR mmu-pri-miR-101 |
| pri-miR-101 R | GGAAGAGTGGTGAACACAGGA (SEQ ID NO: 24) | To PCR mmu-pri-miR-101 |
| pri-miR-451 F | AGTCTGGGTACCCCACCTCCAGAG (SEQ ID NO: 25) | To PCR mmu-pri-miR-451 |
| pri-miR-451 R | GCACAGTGAAGAGGAAAATGTACCC (SEQ ID NO: 26) | To PCR mmu-pri-miR-451 |
| pri-miR-194 F | AGGTACAGGCTAGGTCTTGTCC (SEQ ID NO: 27) | To PCR mmu-pri-miR-194 |
| pri-miR-194 R | AGCTCCGTGCTCCGTAGTCT (SEQ ID NO: 28) | To PCR mmu-pri-miR-194 |
| pri-miR-30a F | GTGTTTGACACTTAGTAGATGA (SEQ ID NO: 29) | To PCR mmu-pri-miR-30a |
| pri-miR-30a R | AATATATTTCTTTGCTTAGC (SEQ ID NO: 30) | To PCR mmu-pri-miR-30a |
| pri-miR-155 F | TTTCTCTTTGCAGGTGCTGC (SEQ ID NO: 31) | To PCR mmu-pri-miR-155 |
| pri-miR-155 R | GTCTGACATCTACGTTCATC (SEQ ID NO: 32) | To PCR mmu-pri-miR-155 |
| shApob | TGACTTTCATCTGTACTACATTCAAGAGATGTAGTACAGATGAAAGTCA GCTTTTT (SEQ ID NO: 33) | To silence mouse Apob gene |
| shPC-1 | CGGGATTCTACCAGATATCTATTCAAGAGATAGATATCTGGTAGAATCC CGTTTTT (SEQ ID NO: 2) | To silence mouse PC-1 gene |
| shSOD1 | CATCATCAATTTCGAGCAGAATTCAAGAGATTCTGCTCGAAATTGATGA TGTTTTT (SEQ ID NO: 1) | To silence human SOD1 gene |
| Apob sensor-F | CGCCTCGAGAAATTGAAGAAGATCTGTTAAC (SEQ ID NO: 34) | o generate partial Apob CDS as shApob sensor element |

TABLE 1-continued

Sequences

| Oligonucleotides | Sequences (5' to 3') | Purpose |
| --- | --- | --- |
| Apob sensor-R | CGCGCGGCCGCTCTTCTCTGGAGGGGACTGT (SEQ ID NO: 35) | o generate partial Apob CDS as shApob sensor element |
| PC-1 sensor-F | CGCCTCGAGCCCAAAATGAATGCTTCTTTCTCG (SEQ ID NO: 36) | To generate partial PC-1 CDS as shPC-1 sensor element |
| PC-1 sensor-R | CGCGCGGCCGCCCTGAAGAATCTGGTTCTTC (SEQ ID NO: 37) | To generate partial PC-1 CDS as shPC-1 sensor element |
| hSOD1 sensor-F | ATAACTCGAGCGAAGGCCGTGTGCGTGCTGAAGGGC (SEQ ID NO: 38) | To generate partial SOD1 CDS as shSOD1 sensor element |
| hSOD1 sensor-R | GCCAGCGGCCGCTTGGGCGATCCCAATTACACCACAAG (SEQ ID NO: 39) | To generate partial SOD1 CDS as shSOD1 sensor element |
| shApobmiR-33 gBlock | AGATCTAGGGCTCTGCGTTTGCTCCAGGTAGTCCGCTGCTCCCTTGGGCCTGGGCCCACTGACAGCCCTGGTGCCTCTGGCCGGCTGCACACCTCCTGGCGGGCAGCTGTGTGTAGTACAGATGAAAGTCAGTGTTCTGGCAATACCTGCTGACTTTACTATGTACTACACACGGAGGCCTGCCCTGACTGCCCACGGTGCCGTGGCCAAAGAGGATCTAAGGGCACCGCTGAGGGCCTACCTAACCATCGTGGGGAATAAGGACAGTGTCACCCTTTTTCTGCAG (SEQ ID NO: 40) | To silence mouse Apob gene |
| shPC-1miR-33 gBlock | AGATCTAGGGCTCTGCGTTTGCTCCAGGTAGTCCGCTGCTCCCTTGGGCCTGGGCCCACTGACAGCCCTGGTGCCTCTGGCCGGCTGCACACCTCCTGGCGGGCAGCTGTGTAGATATCTGGTAGAATCCCGTGTTCTGGCAATACCTGCGGGATTCGCCAAGATATCTACACGGAGGCCTGCCCTGACTGCCCACGGTGCCGTGGCCAAAGAGGATCTAAGGGCACCGCTGAGGGCCTACCTAACCATCGTGGGGAATAAGGACAGTGTCACCCTTTTTCTGCAG (SEQ ID NO: 4) | To silence mouse PC-1 gene |
| shSOD1miR-33 gBlock | AGATCTAGGGCTCTGCGTTTGCTCCAGGTAGTCCGCTGCTCCCTTGGGCCTGGGCCCACTGACAGCCCTGGTGCCTCTGGCCGGCTGCACACCTCCTGGCGGGCAGCTGTGTTCTGCTCGAAATTGATGATGTGTTCTGGCAATACCTGCATCATCATATCCGAGCAGAACACGGAGGCCTGCCCTGACTGCCCACGGTGCCGTGGCCAAAGAGGATCTAAGGGCACCGCTGAGGGCCTACCTAACCATCGTGGGGAATAAGGACAGTGTCACCCTTTTTCTGCAG (SEQ ID NO: 3) | To silence SOD1 gene |
| Apob-F | GTCCAGGTTGAATCACGGGT (SEQ ID NO: 41) | qRT-PCR for Apob mRNA |
| Apob-R | AGGATCCTGCAAGGTCAAGC (SEQ ID NO: 42) | qRT-PCR for Apob mRNA |
| PC-1-F | AAAGGCCGCTGCTTTGAAAG (SEQ ID NO: 43) | qRT-PCR for PC-1 mRNA |
| PC-1-R | CCGCACCTGAATTTGTTGCA (SEQ ID NO: 44) | qRT-PCR for PC-1 mRNA |
| Actin-F | ATGCCAACACAGTGCTGTCTGG (SEQ ID NO: 45) | qRT-PCR for Actin mRNA |
| Actin-R | TGCTTGCTGATCCACATCTGCT (SEQ ID NO: 46) | qRT-PCR for Actin mRNA |

TABLE 1-continued

Sequences

| Oligonucleotides | Sequences (5' to 3') | Purpose |
|---|---|---|
| EGFP-F | AGCAAAGACCCCAACGAGAA (SEQ ID NO: 47) | Quantification of AAV vector preparations |
| EGFP-R | GGCGGCGGTCACGAA (SEQ ID NO: 48) | Quantification of AAV vector preparations |
| EGFP-probe | 6FAM-CGCGATCACATGGTCCTGCTGG-TAMRA (SEQ ID NO: 49) | Small RNA Northern blot |
| shApob AS probe | GACTTTCATCTGTACTACA (SEQ ID NO: 50) | Small RNA Northern blot |
| U6 probe | CTCTGTATCGTTCCAATTTTAGTATA (SEQ ID NO: 51) | Small RNA Northern blot |

What is claimed is:

1. An rAAV vector comprising a transgene engineered to express an inhibitory nucleic acid comprising:
   (i) a pri-miRNA scaffold; and
   (ii) a guide strand that targets SOD1;
   wherein the guide strand that targets SOD1 is encoded by an isolated nucleic acid comprising the sequence set forth in SEQ ID NO: 1.

2. The rAAV vector of claim 1, wherein the pri-miRNA scaffold is selected from pri-miR-122, pri-miR-33, pri-miR-26a, pri-miR-126, pri-miR-22, pri-miR-199, pri-miR-99, pri-miR-21, pri-miR-375, pri-miR-101, pri-miR-451, pri-miR-194, pri-miR-30a, and pri-miR-155.

3. The rAAV vector of claim 1, wherein the transgene comprises the sequence set forth in SEQ ID NO: 3.

4. The rAAV vector of claim 1, wherein the rAAV vector is a self-complementary AAV (scAAV) vector.

5. An rAAV comprising the rAAV vector of claim 1 and an AAV capsid protein.

6. A method of reducing expression of SOD1 in a cell, the method comprising administering the rAAV of claim 5 to the cell.

7. A method for treating amyotrophic lateral sclerosis (ALS) in a subject in need thereof, the method comprising administering to the subject the rAAV of claim 5.

8. The rAAV of claim 5, wherein the AAV capsid protein is an AAV9 capsid protein.

* * * * *